United States Patent
Fernando et al.

(10) Patent No.: US 11,325,909 B2
(45) Date of Patent: May 10, 2022

(54) CRYSTALLINE 2-AMINO-2-(HYDROXYMETHYL)PROPANE-1,3-DIOL SALT OF 4-(4-(1-ISOPROPYL-7-OXO-1,4,6,7-TETRAHYDROSPIRO[INDAZOLE-5,4'-PIPERIDINE]-1'-CARBONYL)-6-METHOXYPRYRIDIN-2-YL)BENZOIC ACID

(71) Applicant: Pfizer Inc., New York, NY (US)

(72) Inventors: Dilinie Fernando, Jamaica Plain, MA (US); Shawn Marie LaCasse, Griswold, CT (US); Kristin Elizabeth Price Wiglesworth, Germantown, MD (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 16/765,350

(22) PCT Filed: Nov. 14, 2018

(86) PCT No.: PCT/IB2018/058966
§ 371 (c)(1),
(2) Date: May 19, 2020

(87) PCT Pub. No.: WO2019/102311
PCT Pub. Date: May 31, 2019

(65) Prior Publication Data
US 2020/0354362 A1 Nov. 12, 2020

Related U.S. Application Data

(60) Provisional application No. 62/589,256, filed on Nov. 21, 2017.

(51) Int. Cl.
*C07D 471/10* (2006.01)

(52) U.S. Cl.
CPC ........ *C07D 471/10* (2013.01); *C07B 2200/13* (2013.01)

(58) Field of Classification Search
None
See application file for complete search history.

(56) References Cited

U.S. PATENT DOCUMENTS 8,859,577 B2 * 10/2014 Didiuk ................. A61P 3/10
514/278

FOREIGN PATENT DOCUMENTS

| RU | 2374256 | 11/2009 |
|---|---|---|
| RU | 2540337 | 2/2015 |
| WO | 2005090367 | 9/2005 |
| WO | 2011058474 | 5/2011 |
| WO | 2012042433 | 4/2012 |
| WO | 2012056372 | 5/2012 |
| WO | 2012143813 | 10/2012 |

OTHER PUBLICATIONS

International Written Opinion and Search Report dated Nov. 14, 2018 for Application No. PCT/IB2018/058966, filed on Jan. 9, 2019, 15 pages.
Saal, C, et al., "Pharmaceutical salts: A summary on doses of salt formers from the Orange Book", European Journal of Pharmaceutical Sciences, Jun. 5, 2013, pp. 614-623, 49(4).
Bastin, Richard J., et al., "Salt selection and Optimisation Procedures for Pharmaceutical New Chemical Entities", Organic Process Research & Development, 2000, pp. 427-435,4(5).
International Patent Application, PCT/IB2018/058966, filed Nov. 14, 2018, International Preliminary Reporton Patentability, dated May 26, 2020, 8 pages.
Morissette, Sherry L., et al., "High-throughput crystallization: polymorphs, salts, co-crystals and solvates of pharmaceutical solids", Advanced Drug Delivery Review, 2004, pp. 275-300, 56(3).
Paulekuhn, Steffen G , et al., "Trends in Active Pharmaceutical Ingredient Salt Selection based on Analysis of the Orange Book Database", Journal Medicinal Chemistry, 2007, pp. 6665-6672, 50(26).
Serajuddin, Abu T.M., et al., "Salt formation of improve drug solubility", Advanced Drug Reviews, 2007, pp. 303-616, 59(7).
Russian Application No. 2020116458, Office Action and Search Report, dated Nov. 20, 2020, 2 pages.
Russian Application No. 2020116458, Office Action, dated Jun. 1, 2021, 10 pages.

* cited by examiner

*Primary Examiner* — Craig D Ricci
(74) *Attorney, Agent, or Firm* — Richard V. Zanzalari

(57) ABSTRACT

The invention provides the tris salt of 4-(4-(1-isopropyl-7-oxo-1,4,6,7-tetrahydrospiro[indazole-5,4'-piperidine]-1'-carbonyl)-6-methoxypyridin-2-yl)benzoic acid as a crystalline anhydrous or tri-hydrate; as well as polymorphs, pharmaceutical compositions, dosage forms, and the use thereof in treating diseases, conditions or disorders modulated by the inhibition of an acetyl-CoA carboxylase (ACC) enzyme(s) in an animal.

11 Claims, 7 Drawing Sheets

CRYSTALLINE 2-AMINO-2-(HYDROXYMETHYL)PROPANE-1,3-DIOL SALT OF 4-(4-(1-ISOPROPYL-7-OXO-1,4,6,7-TETRAHYDROSPIRO[INDAZOLE-5,4'-PIPERIDINE]-1'-CARBONYL)-6-METHOXYPRYRIDIN-2-YL)BENZOIC ACID

This application is a national stage application under 35 U.S.C. 371 of PCT/162018/058966, filed on Nov. 14, 2018, which claims the benefit of U.S. Provisional Patent Application No. 62/589,256, filed on Nov. 21, 2017, the disclosures of which are hereby incorporated by reference in their entirety.

FIELD OF THE INVENTION

The invention provides the tris salt of 4-(4-(1-isopropyl-7-oxo-1,4,6,7-tetrahydrospiro[indazole-5,4'-piperidine]-1'-carbonyl)-6-methoxypyridin-2-yl)benzoic acid; as well as crystalline forms, polymorphs, pharmaceutical compositions, dosage forms, and the use thereof in treating diseases, conditions or disorders modulated by the inhibition of an acetyl-CoA carboxylase (ACC) enzyme(s) in an animal.

BACKGROUND OF THE INVENTION 4-(4-(1-Isopropyl-7-oxo-1,4,6,7-tetrahydrospiro[indazole-5,4'-piperidine]-1'-carbonyl)-6-methoxypyridin-2-yl)benzoic acid (referred to herein as Compound 1) is a selective ACC inhibitor and was prepared as the free acid in Example 9 of U.S. Pat. No. 8,859,577, which is the U.S. national phase of International Application No. PCT/IB2011/054119, all of which are hereby incorporated herein by reference in their entireties for all purposes. Compound 1, as the free acid, has unsuitable physicochemical characteristics.

Salt formation provides a means of altering the physicochemical and resultant biological characteristics of a drug without modifying its chemical structure. A salt form can have a dramatic influence on the properties of the drug. The selection of a suitable salt form involves evaluation of many factors, including whether any salt can be formed. Other factors included in this selection include hygroscopicity, stability, solubility, and the process profile of any salt form that might be discovered.

Nonalcoholic fatty liver disease (NAFLD) is the hepatic manifestation of metabolic syndrome, and is a spectrum of hepatic conditions encompassing steatosis, non-alcoholic steatohepatitis (NASH), fibrosis, cirrhosis and ultimately hepatocellular carcinoma. NAFLD and NASH are considered the primary fatty liver diseases as they account for the greatest proportion of individuals with elevated hepatic lipids. The severity of NAFLD/NASH is based on the presence of lipid, inflammatory cell infiltrate, hepatocyte ballooning, and the degree of fibrosis. Although not all individuals with steatosis progress to NASH, a substantial portion do.

It is becoming increasingly clear that hepatic lipid accumulation causes hepatic insulin resistance and contributes to the pathogenesis of type 2 diabetes (T2D). Savage, et al., demonstrated that ACC1 and ACC2 are both involved in regulating fat oxidation in hepatocytes while ACC1, the dominant isoform in rat liver, is the sole regulator of fatty acid synthesis. Furthermore, in their model, combined reduction of both isoforms is required to significantly lower hepatic malonyl-CoA levels, increase fat oxidation in the fed state, reduce lipid accumulation, and improve insulin action in vivo. Thus, hepatic ACC1 and ACC2 inhibitors may be useful in the treatment of NAFLD and hepatic insulin resistance. See, Savage, D. B., et al., "Reversal of diet-induced hepatic steatosis and hepatic insulin resistance by antisense oligonucleotide inhibitors of acetyl-CoA carboxylases 1 and 2" *J. Clin. Invest.* 2006; 116(3):817-24. See also, Oh, W., et al., "Glucose and fat metabolism in adipose tissue of acetyl-CoA carboxylase 2 knockout mice" *PNAS*, 102(5) 1384-1389 (2005).

Consequently, there is a need for oral medicaments containing ACC1 and/or ACC2 inhibitors to treat diseases including NAFLD, NASH, and T2D.

SUMMARY OF THE INVENTION

The invention provides crystalline polymorphs of the tris salt of 4-(4-(1-isopropyl-7-oxo-1,4,6,7-tetrahydrospiro[indazole-5,4'-piperidine]-1'-carbonyl)-6-methoxypyridin-2-yl)benzoic acid, referred to herein as Compound 1, wherein the crystalline salt may be anhydrous or a hydrate, more specifically, a trihydrate; as well as polymorphs, pharmaceutical compositions, dosage forms, and the use thereof in treating diseases, conditions or disorders modulated by the inhibition of an acetyl-CoA carboxylase (ACC) enzyme(s) in an animal. The novel crystalline forms of the present invention have properties which are particularly suitable for use as a drug, including improved solubility, and bioavailability.

Solid crystalline forms of Compound 1 are disclosed herein, wherein each solid form can be uniquely identified by several different analytical parameters, alone or in combination, such as, but not limited to: powder X-ray diffraction pattern peaks or combinations of two or more peaks; solid-state NMR $^{13}$C chemical shifts or combinations of two or more chemical shifts; and Raman peak shift or combinations of two or more Raman peak shifts.

DETAILED DESCRIPTION OF THE INVENTION

Figure 1:
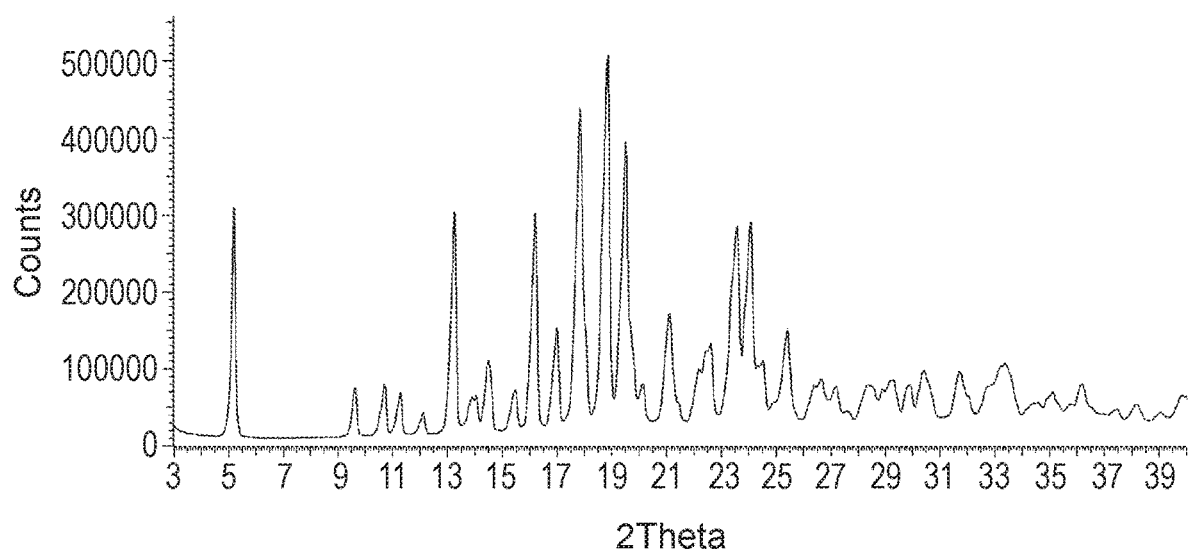
FIG. 1 shows an illustrative PXRD pattern of Form 1 carried out on a Bruker AXS D4 Endeavor diffractometer equipped with a Cu radiation source.

Compound 1 contains two ionizable sites: the nitrogen on the pyridine ring and the carboxylic acid. The invention provides a crystalline tris salt of Compound 1 (4-(4-(1-Isopropyl-7-oxo-1,4,6,7-tetrahydrospiro[indazole-5,4'-piperidine]-1'-carbonyl)-6-methoxypyridin-2-yl)benzoic acid). The invention concerns the mono-tris salt of Compound 1. There are two crystalline forms of the mono-tris salt: Form 1 is an anhydrous crystalline solid and Form 2 is a trihydrate crystalline solid. Form 3 is an amorphous form.

Definitions

The term "tris" means 2-amino-2-(hydroxymethyl)propane-1,3-diol, also known as THAM and tromethamine. The tris salt of Compound 1 means a salt of Compound 1 made using 2-amino-2-(hydroxymethyl)propane-1,3-diol. Tris is associated with the carboxylic acid moiety of Compound 1. Unless otherwise stated, when referencing the tris salt of Compound 1, the counterion and Compound 1 are in a stoichiometric ratio of about 1:1.

The term "Form 1" means the anhydrous crystalline 2-amino-2-(hydroxymethyl)propane-1,3-diol (tris) salt of Compound 1 as the mono-tris salt. It is intended that Form 1 is free of water, but residual solvent, including water, could be present if the material is not dried completely.

The term "Form 2" means the trihydrate crystalline 2-amino-2-(hydroxymethyl)propane-1,3-diol (tris) salt of Compound 1 as the mono-tris salt.

The term "trihydrate" as used herein refers to the inclusion of about three water molecules.

The term "about" generally means within 10%, preferably within 5%, and more preferably within 1% of a given value or range. Alternatively, the term "about" means within an acceptable standard error of the mean, when considered by one of ordinary skill in the art.

G or g is gram, and mg means milligram.
H or h means hour.
IPA means isopropyl alcohol.
L is liter.
mL is milliliter.
MCC means microcrystalline cellulose.
RH means relative humidity.
RT or rt means room temperature which is the same as ambient temperature (about 20 to 25° C.).

$^1$H Nuclear magnetic resonance (NMR) spectra were in all cases consistent with the proposed structures. Characteristic chemical shifts (δ) are given in parts-per-million (ppm) relative to the residual proton signal in the deuterated solvent (CHCl$_3$ at 7.27 ppm; CD$_2$HOD at 3.31 ppm) and are reported using conventional abbreviations for designation of major peaks: e.g. s, singlet; d, doublet; t, triplet; q, quartet; m, multiplet; br, broad.

ssNMR means solid-state NMR.
PXRD means Powder X-ray Diffraction.
RH means relative humidity.

The term "substantially the same" when used to describe X-ray powder diffraction patterns is mean to include patterns in which peaks are within a standard deviation of +/−0.2° 2θ.

As used herein, the term "substantially pure" with reference to a particular crystalline form means that the crystalline form includes less than 10%, preferably less than 5%, preferably less than 3%, preferably less than 1% by weight of any other physical form of Compound 1.

Very few counterions were evaluated to form a salt at the nitrogen of Compound 1 because of the low pKa and the poor results, e.g., a very hygroscopic solid was obtained using sulfuric acid as the counterion.

Many counterions investigated did not give a salt form, but the free acid upon isolation: histidine, lysine (with Na and Ca), L-ornithine (with Na). Attempts to use arginine (with Na) resulted in the free acid because of dissociation upon drying. Results from evaluating many counterions is shown in Table 1. The salts were obtained by adding stock solution of Compound 1 to the counterion source, in about 1:1 ratio with Compound 1. The calculated amount of counterion to give a 1:1 molar ratio with Compound 1 (as the free acid) is provided in parentheses in the column identifying the counterion. The actual amount of counterion added is provided in parentheses where the results are provided for each counterion in the different solvents. A stock solution of Compound 1 (as the free acid) in a given solvent was prepared and added to the counterion in the given solvent and then additional solvent was added to give a total volume provided in parentheses below the solvent in Table 1. Each sample was observed for a week, during which the sample was heated to about 50° C. for about 3 hr and allowed to cool to rt with stirring. For the experiments in which methanol (MeOH), ethanol (EtOH), and isopropyl acetate/ethyl acetate (IPAC/EtOAc), the sample was observed for a total of three weeks. Table 1 provides what was observed during this time. For some samples, 2 mL of heptanes were added after the first week, and this is identified with an * in Table 1. For methanol and acetonitrile (ACN), the stock solution was 15 mg/mL. For ethanol, the stock solution was 30 mg/mL. For IPAC/EtOAc, the stock solution was 13.6 mg/mL in 50 mL IPAC/5 mL EtOAc including a few drops of water. The total volume (vol.) is provided in parentheses below each listed solvent examined.

TABLE 1

| | Salt Evaluation | | | |
|---|---|---|---|---|
| Counter Ion Source | Methanol (total vol. 3.0 ml) | Ethanol (total vol. 1.5 ml, excluding heptanes*) | Acetonitrile (total vol. 3.0 ml) | IPAC:EtOAc (10:1) (total vol. 3.5 ml, excluding heptanes*) |
| Calcium hydroxide (8.1 mg) | Crystalline to amorphous solid (8.5 mg) | Amorphous solid (10.4 mg) | Solid, some crystalline (8.8 mg) | Crystalline solid (8.1 mg) |
| Calcium methoxide (11.5 mg) | Mostly Amorphous solid, few crystals (11.5 mg) | Amorphous solid (11.2 mg) | Mostly Amorphous solid, few crystals (11.6 mg) | Crystalline solid (11.5 mg) |
| Choline hydroxide (22.8 mg) | No solid formed (25.5 mg) | No solid formed* (29.0 mg) | No solid formed (23.2 mg) | Solid with few crystals (22.3 mg) |
| Dibenzylethyl-enediamine (27.1 mg) | No solid formed (29.0 mg) | No solid formed* (29.1 mg) | No solid formed (24.9 mg) | Gum* (28.0 mg) |

TABLE 1-continued

Salt Evaluation

| Counter Ion Source | Methanol (total vol. 3.0 ml) | Ethanol (total vol. 1.5 ml, excluding heptanes*) | Acetonitrile (total vol. 3.0 ml) | IPAC:EtOAc (10:1) (total vol. 3.5 ml, excluding heptanes*) |
|---|---|---|---|---|
| Diethylamine (8.1 mg) | No solid formed (8.0 mg) | No solid formed* (8.0 mg) | Crystalline solid (8.0 mg) | No solid formed* (10.0 mg) |
| Diethanol-amine (11.7 mg) | No solid formed (12.0 mg) | No solid formed* (12.8 mg) | Crystalline solid (14.8 mg) | Gum/Sticky Solid* (11.7 mg) |
| L-Lysine (16.5 mg) | No solid formed (17.9 mg) | Solid with few crystals (16.3 mg) | Thick solid (16.9 mg) | Mostly Amorphous solid, few crystals (17.5 mg) |
| Meglumine (21.6 mg) | No solid formed (23.3 mg) | No solid formed* (21.9 mg) | Gum (22.3 mg) | White solid, partial crystalline (21.6 mg) |
| Piperazine (9.4 mg) | No solid formed (10.3 mg) | No solid formed* (10.0 mg) | No solid formed (11.0 mg) | White solid crystalline* (9.4 mg) |
| Potassium hydroxide (6.1 mg) | Not examined | No solid formed* (6.5 mg) | Gum (6.2 mg) | Amorphous solid* (6.5 mg) |
| Sodium hydroxide (4.4 mg) | No solid formed (6.4 mg) | Amorphous solid* (4.9 mg) | Amorphous solid (5.2 mg) | Crystalline solid* (4.6 mg) |
| Tris (13.3 mg) | No solid formed (16.6 mg) | No solid formed* (14.5 mg) | Gum (14.6 mg) | Some white solid crystalline (14.7 mg) |

*Added 2 mL of heptanes after the first week.

Determining whether a solid would form was just one factor in this evaluation. Although crystalline solids formed when making salts using calcium, potassium, and sodium, the crystalline solids were too hygroscopic to continue the evaluation. Hygroscopicity data was not obtained for many of these salts because it was observed mainly through visualization. For example, as the calcium and potassium salt forms were being collected on filter paper, the solid material turned to a gum. Compound 1 as the choline salt was isolated; hygroscopicity was found to be more than 20% weight change at 30% relative humidity. Moreover, although a solid was obtained for the salts of diethanolamine, diethylamine, and piperazine, these salts were not pursued. See, e.g., C. Saal, A. Becker, Euro. J. of Pharm Sci 49 (2013) 614-623; Paullekuhn, G Steffen, et al, J. Med. Chem. 2007, 50, 6665-6682.

Furthermore, although a solid was obtained, additional evaluation, like $^1$H NMR was used to determine whether a salt actually formed. In some instances, the solid obtained was Compound 1 (as the free acid) and not associated with the counterion.

At ambient temperature with RH above 20%, Form 2 is the more stable form between Form 1 and Form 2. Solvent conditions affect whether Form 1 or Form 2 is obtained. It was determined that a critical water activity of 0.2 in IPA/water provides crystalline Form 2. The following solvents, when used in the presence of water, provide Form 2: 5% to 15% water/acetone, 4% water/96% acetonitrile, 1% water/99% butyl acetate, 1% water/99% isopropyl acetate, 1% water/99% ethyl acetate, 2% water/98% dichloroethylene, 2% water/98% methyl ethyl ketone, 3 to 6.0% water/97 to 94% 2-methyltetrahydrofuran, and 4% water/96% n-propanol.

Compound 1 also faced challenges regarding solubility. Table 2 provides the solubility of Compound 1 (as the free acid) and various salts. Compound 1 (as the free acid) proved to be an unacceptable form for making a dosage form for routine oral administration. Although Compound 1 (as the free acid) was crystalline, thermodynamic solubility was not consistent. The calcium salt had an extremely low solubility at low pH.

TABLE 2

Thermodynamic Solubility of Compound 1 and Salt forms

| Compound 1 | Solubility (μM) pH 1.2 | Solubility (μM) pH 6.5 | Solubility (μM) pH 7.4 |
|---|---|---|---|
| Free acid - batch A | 11.8 (avg, n = 2, 11.6 and 12.1) | 44.7 (avg, n = 2, 39.0 and 50.5) | 255.0 (avg, n = 2, 237.0 and 273.0) |
| Free acid - batch B | 13.0 (avg, n = 2, 7.8 and 18.3) | 222.0 (avg, n = 2, 245.0 and 199.0) | 1700.0 (avg, n = 2, 1750.0 and 1650.0) |
| Free acid - batch C | <0.5 | 19.6 | 194.0 |
| Calcium | 13.5 | 1500.0 | 5050.0 |
| Choline - batch A | 1400.0 | 1810.0 | 4640.0 |
| Choline - batch B | 2850.0 | 7440.0 | 6170.0 |
| Diethylamine | 1850.0 | 4880.0 | 7340.0 |
| Diethanolamine | 2770.0 | 3500.0 | 6530.0 |
| Piperazine | 1800.0 | 1110.0 | 4390.0 |
| Tris (Form 1) | 1320.0 | 3980.0 | 4770.0 |

A salt form was pursued because Compound 1 (as the free acid) did not provide a consistent result; without limitation, it was thought that the free acid might exist as multiple non-stoichiometric hydrates/solvates. As seen in Table 2, the solubility of the free acid varied among the three batches at each pH.

Additional work was done comparing the free acid and tris salts in pharmacokinetic studies as provided in Table 3. The mono-tris salt of Compound 1, whether it was Form 1 or Form 2, had similar pharmacokinetics. The mono-tris salt of Compound 1 had much better pharmacokinetics than Compound 1 (as the free acid). Although the suspension was prepared with the anhydrous Form 1, trihydrate Form 2 would also likely be present given the aqueous media. The form present in the suspension was not identified.

TABLE 3

Pharmacokinetics of Select Forms of Compound 1

| Form of Compound 1 Used to Prepare Oral Formulation | Oral Formulation | Dose (mg/kg) | AUC/Dose (ng*h/ml/mpk) |
|---|---|---|---|
| Form 1 | Immediate Release Tablet | 2 | 5750 |
| Form 2 | Immediate Release Tablet | 2 | 5650 |
| Form 1 | Suspension | 5 | 7240 |
| Free acid of Compound 1 | Suspension | 10 | 4120 |

Form 1 is anhydrous and is thermodynamically stable below a water activity of about 0.2 (20% RH) at ambient temperature. Form 1 has a PXRD pattern substantially the same as that shown in FIG. 1. Characteristic PXRD peaks of Form 1, expressed as 2θ±0.2° 2θ are at 9.6, 10.7, and 11.3. Peak locations and intensities for the PXRD pattern in FIG. 1 are provided in Table 4.

TABLE 4

PXRD Peaks and Relative Intensities of Form 1

| Degrees 2Θ ± 0.2° 2Θ | Relative Intensity (%) |
|---|---|
| 5.2 | 62 |
| 9.6 | 13 |
| 10.7 | 14 |
| 11.3 | 11 |
| 12.1 | 6 |
| 13.3 | 60 |
| 13.9 | 9 |
| 14.0 | 10 |
| 15.5 | 11 |
| 16.2 | 58 |
| 17.0 | 27 |
| 17.8 | 86 |
| 18.9 | 100 |
| 19.5 | 77 |
| 20.1 | 11 |
| 21.1 | 29 |
| 22.2 | 15 |
| 22.4 | 19 |
| 22.6 | 21 |
| 23.6 | 53 |
| 24.1 | 54 |
| 24.5 | 16 |
| 25.4 | 25 |
| 26.4 | 9 |
| 26.6 | 11 |
| 27.2 | 9 |
| 28.3 | 9 |
| 29.3 | 10 |

TABLE 4-continued

PXRD Peaks and Relative Intensities of Form 1

| Degrees 2Θ ± 0.2° 2Θ | Relative Intensity (%) |
|---|---|
| 29.9 | 9 |
| 30.4 | 13 |
| 31.7 | 13 |
| 33.4 | 15 |

Figure 2:
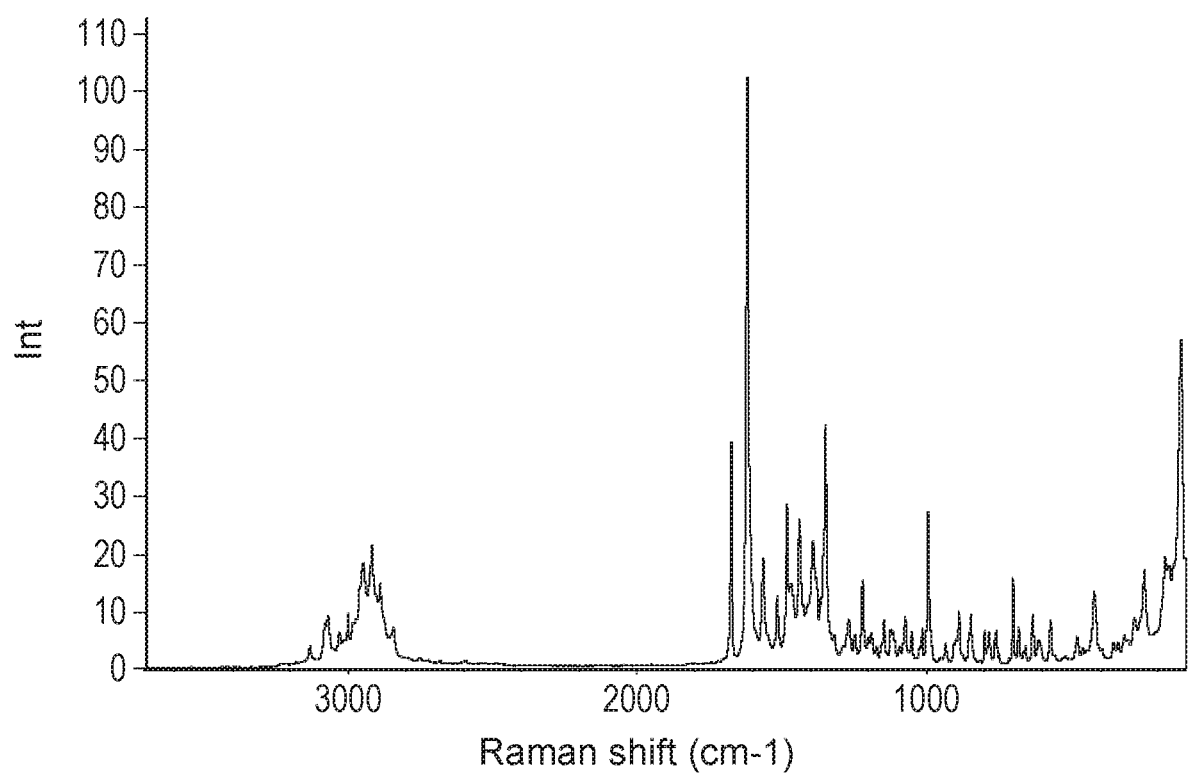
FIG. 2 shows an illustrative Raman spectra of Form 1 collected using a Nicolet NXR FT-Raman accessory attached to the FT-IR bench.

Form 1 has a Raman spectrum substantially the same as that shown in FIG. 2. Form 1 has characteristic Raman peak shifts, expressed as cm$^{-1}$, at 568, 698, 989, 1218, 1511, 1561, and 1615, ±2 cm$^{-1}$. Peak positions (±2 cm$^{-1}$) and normalized intensity (W=weak, M=medium, S=strong) of Form 1 in FIG. 2 are listed in Table 5.

TABLE 5

Raman Peaks and Normalized Intensity of Form 1

| Raman Peak Position (cm$^{-1}$) | Normalized Intensity |
|---|---|
| 115 | M |
| 156 | W |
| 170 | W |
| 241 | W |
| 274 | W |
| 311 | W |
| 334 | W |
| 350 | W |
| 417 | W |
| 456 | W |
| 476 | W |
| 568 | W |
| 608 | W |
| 628 | W |
| 653 | W |
| 678 | W |
| 698 | W |
| 755 | W |
| 779 | W |
| 794 | W |
| 842 | W |
| 885 | W |
| 929 | W |
| 989 | W |
| 1011 | W |
| 1047 | W |
| 1071 | W |
| 1090 | W |
| 1119 | W |
| 1143 | W |
| 1169 | W |
| 1187 | W |
| 1196 | W |
| 1218 | W |
| 1244 | W |
| 1265 | W |
| 1315 | W |
| 1345 | M |
| 1363 | W |
| 1388 | W |
| 1435 | W |
| 1466 | W |
| 1478 | W |
| 1511 | W |
| 1561 | W |
| 1615 | S |
| 1671 | M |
| 2840 | W |
| 2885 | W |
| 2914 | W |
| 2945 | W |
| 2998 | W |
| 3027 | W |

TABLE 5-continued

Raman Peaks and Normalized Intensity of Form 1

| Raman Peak Position (cm$^{-1}$) | Normalized Intensity |
|---|---|
| 3066 | W |
| 3129 | W |

Figure 3:
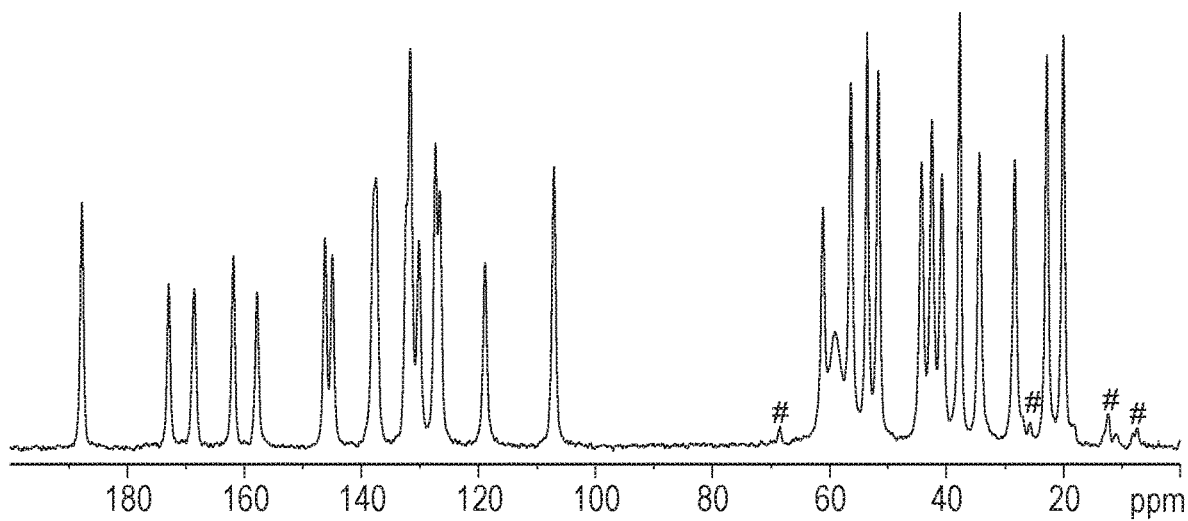
FIG. 3 shows an illustrative $^{13}$C ssNMR pattern of Form 1 conducted on a Bruker-BioSpin CPMAS probe positioned into a Bruker-BioSpin Avance III 500 MHz ($^1$H frequency) NMR spectrometer.

Form 1 has a $^{13}$C ssNMR spectrum substantially the same as that shown in FIG. 3. Form 1 has characteristic $^{13}$C ssNMR chemical shifts, expressed as ppm, at 22.9, 146.2, 157.9, 161.9, and 172.9, ±0.2 ppm. $^{13}$C chemical shifts (±0.2 ppm) of Form 1 as shown in FIG. 3 are listed in Table 6.

TABLE 6

$^{13}$C chemical shifts and Intensity of Form 1

| $^{13}$C chemical shifts (ppm) | Intensity |
|---|---|
| 20.1 | 95 |
| 22.9 | 90 |
| 28.4 | 66 |
| 34.3 | 68 |
| 37.7 | 100 |
| 40.8 | 63 |
| 42.5 | 76 |
| 44.3 | 66 |
| 51.6 | 87 |
| 53.6 | 96 |
| 56.4 | 84 |
| 59.1 | 27 |
| 61.2 | 55 |
| 107.1 | 65 |
| 118.9 | 42 |
| 126.6 | 59 |
| 127.3 | 70 |
| 130.2 | 47 |
| 131.7 | 92 |
| 132.3 | 56 |
| 137.5 | 62 |
| 137.9 | 59 |
| 144.9 | 44 |
| 146.2 | 48 |
| 157.9 | 36 |
| 161.9 | 44 |
| 168.6 | 36 |
| 172.9 | 38 |
| 187.7 | 56 |

Figure 4:
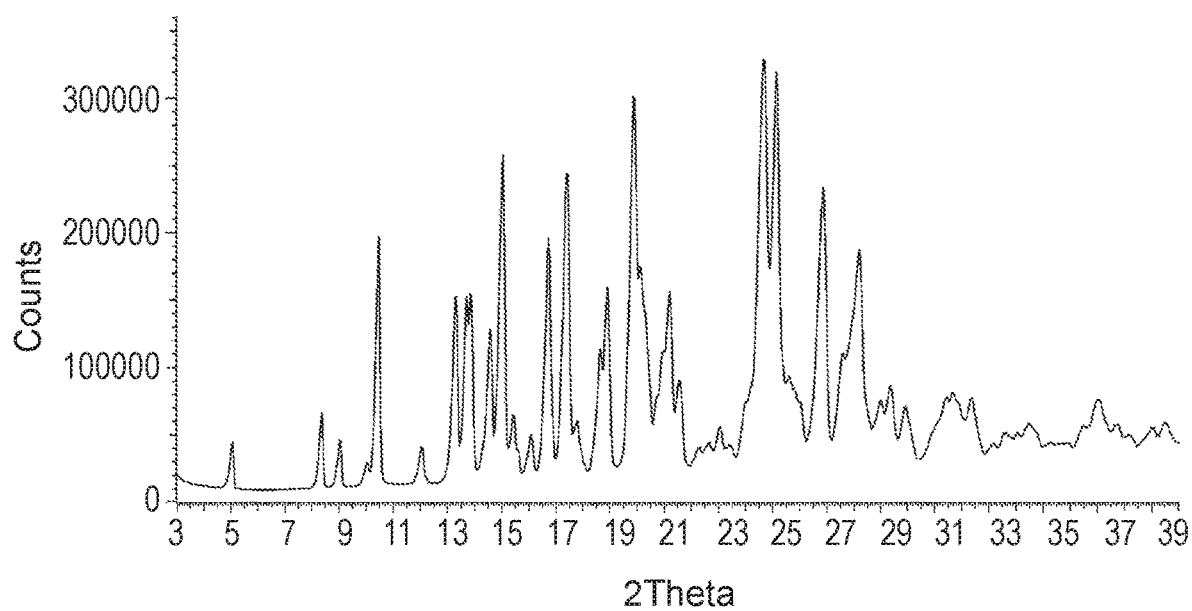
FIG. 4 shows an illustrative PXRD pattern of Form 2 carried out on a Bruker AXS D4 Endeavor diffractometer equipped with a Cu radiation source.

Form 2 is a trihydrate and is thermodynamically stable above a water activity of about 0.2 at ambient temperature and 20% RH. Form 2 has a PXRD pattern substantially the same as that shown in FIG. 4. Characteristic PXRD peaks of Form 2, expressed as 2θ±0.2° 2θ are at 8.4, 9.0, 10.5, 15.0, and 24.7. Peak locations and intensities for the PXRD pattern in FIG. 4 are provided in Table 7.

TABLE 7

PXRD Peaks and Relative Intensities of Form 2

| Degrees 2Θ ± 0.2° 2Θ | Relative Intensity (%) |
|---|---|
| 5.0 | 11 |
| 8.4 | 18 |
| 9.0 | 12 |
| 10.0 | 6 |
| 10.5 | 62 |
| 12.1 | 9 |
| 13.3 | 46 |
| 13.7 | 45 |
| 13.9 | 46 |
| 14.6 | 37 |
| 15.0 | 80 |
| 15.4 | 15 |
| 16.1 | 10 |
| 16.7 | 59 |
| 17.4 | 74 |
| 17.8 | 13 |
| 18.6 | 30 |
| 18.9 | 45 |
| 19.9 | 93 |
| 20.1 | 50 |
| 21.2 | 46 |
| 21.5 | 21 |
| 24.7 | 100 |
| 25.2 | 97 |
| 26.9 | 71 |
| 28.2 | 52 |
| 29.0 | 15 |
| 29.4 | 18 |
| 29.9 | 13 |
| 31.4 | 15 |
| 31.7 | 16 |
| 32.4 | 14 |
| 33.6 | 5 |
| 34.5 | 7 |
| 37.0 | 12 |

Figure 5:
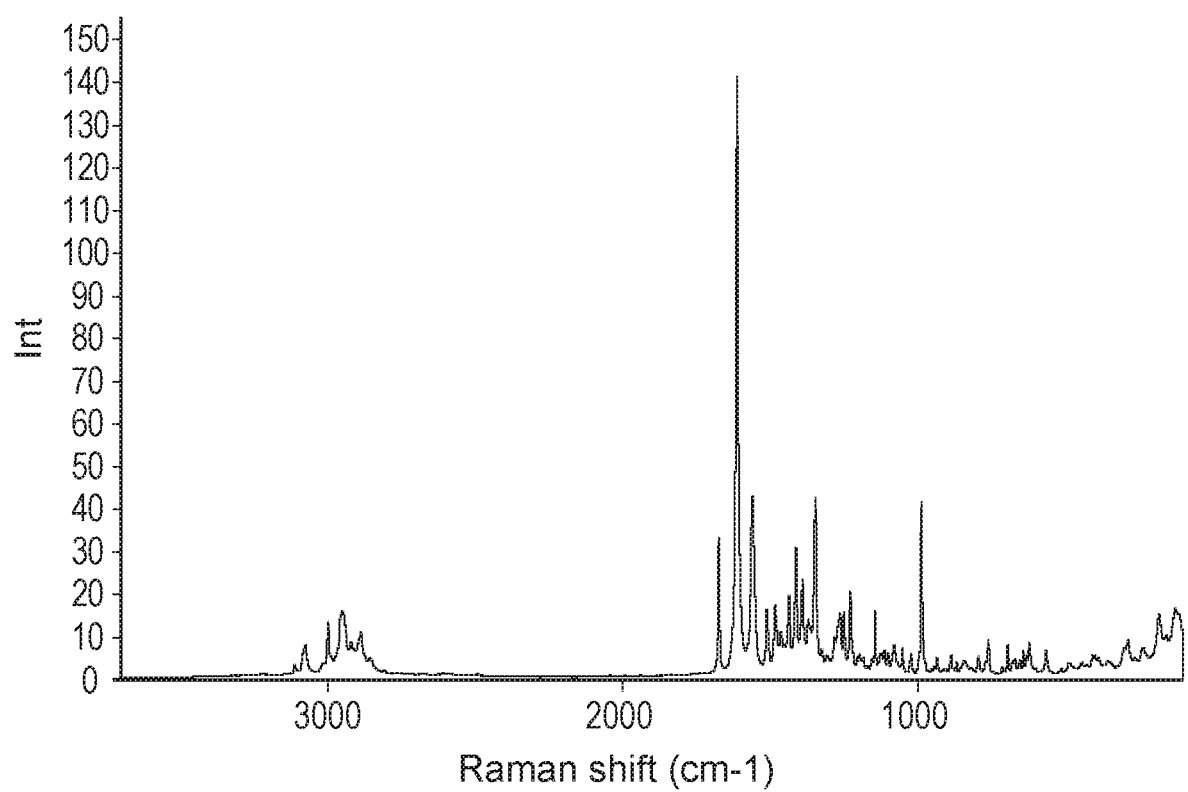
FIG. 5 shows an illustrative Raman spectra of Form 2 collected using a Nicolet NXR FT-Raman accessory attached to the FT-IR bench.

Form 2 has a Raman spectrum substantially the same as that shown in FIG. 5. Form 2 has characteristic Raman peak shift, expressed as cm$^{-1}$, at 562, 692, 984, 1225, 1507, 1557, and 1610±2 cm$^{-1}$. Peak positions (±2 cm$^{-1}$) and normalized intensity (W=weak, M=medium, S=strong) of Form 2 in FIG. 5 are listed in Table 8.

TABLE 8

Raman Peaks and Normalized Intensity of Form 2

| Raman Peak Position (cm$^{-1}$) | Normalized Intensity |
|---|---|
| 123 | W |
| 179 | W |
| 232 | W |
| 284 | W |
| 405 | W |
| 441 | W |
| 481 | W |
| 562 | W |
| 620 | W |
| 628 | W |
| 639 | W |
| 650 | W |
| 667 | W |
| 692 | W |
| 710 | W |
| 758 | W |
| 790 | W |
| 839 | W |
| 864 | W |
| 884 | W |
| 931 | W |
| 984 | W |
| 1019 | W |
| 1048 | W |
| 1077 | W |
| 1097 | W |
| 1109 | W |
| 1118 | W |
| 1140 | W |
| 1194 | W |

TABLE 8-continued

Raman Peaks and Normalized Intensity of Form 2

| Raman Peak Position (cm$^{-1}$) | Normalized Intensity |
|---|---|
| 1225 | W |
| 1246 | W |
| 1261 | W |
| 1277 | W |
| 1305 | W |
| 1321 | W |
| 1344 | W |
| 1369 | W |
| 1387 | W |
| 1410 | W |
| 1433 | W |
| 1460 | W |
| 1480 | W |
| 1507 | W |
| 1557 | M |
| 1610 | S |
| 1670 | W |
| 2884 | W |
| 2916 | W |
| 2946 | W |
| 2995 | W |
| 3073 | W |
| 3108 | W |

Figure 6:
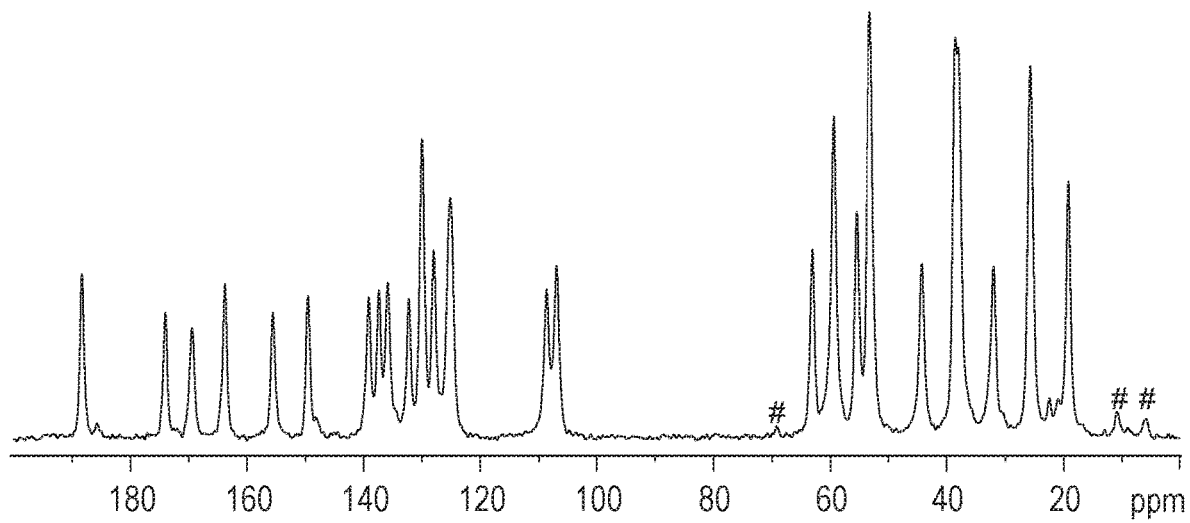
FIG. 6 shows an illustrative $^{13}$C ssNMR pattern of Form 2 conducted on a Bruker-BioSpin CPMAS probe positioned into a Bruker-BioSpin Avance III 500 MHz ($^1$H frequency) NMR spectrometer.

Form 2 has a $^{13}$C ssNMR spectrum substantially the same as that shown in FIG. 6. Form 2 has characteristic $^{13}$C ssNMR chemical shifts, expressed as ppm, at 19.2, 149.5, 155.6, 163.8, and 188.3, ±0.2 ppm. $^{13}$C chemical shifts (±0.2 ppm) of Form 2 as shown in FIG. 6 are listed in Table 9.

TABLE 9

$^{13}$C chemical shifts and Intensity of Form 2

| $^{13}$C chemical shifts (ppm) | Intensity |
|---|---|
| 19.2 | 60 |
| 25.7 | 87 |
| 32.0 | 40 |
| 38.0 | 92 |
| 38.5 | 94 |
| 44.2 | 41 |
| 53.2 | 100 |
| 55.5 | 53 |
| 59.4 | 76 |
| 63.1 | 44 |
| 107.0 | 40 |
| 108.7 | 35 |
| 125.1 | 56 |
| 128.0 | 44 |
| 130.0 | 70 |
| 132.3 | 33 |
| 135.9 | 37 |
| 137.4 | 35 |
| 139.1 | 33 |
| 149.5 | 33 |
| 155.6 | 30 |
| 163.8 | 36 |
| 169.5 | 26 |
| 174.0 | 29 |
| 188.3 | 39 |

Based on the disclosure provided herein, one of ordinary skill in the art would appreciate that each Form 1 and Form 2 can be uniquely identified by several different spectral peaks or patterns in varying combinations. Described below are exemplary combinations of characteristic peak values that can be used to separately identify Form 1 and Form 2 but in no way should these exemplary combinations be viewed as limiting other peak value combinations disclosed herein.

One aspect of the present invention provides a crystalline 2-amino-2-(hydroxymethyl)propane-1,3-diol salt of 4-(4-(1-isopropyl-7-oxo-1,4,6,7-tetrahydrospiro[indazole-5,4'-piperidine]-1'-carbonyl)-6-methoxypyridin-2-yl)benzoic acid (Compound 1).

Another aspect of the present invention provides the crystalline salt of Compound 1, wherein the ratio of 4-(4-(1-isopropyl-7-oxo-1,4,6,7-tetrahydrospiro[indazole-5,4'-piperidine]-1'-carbonyl)-6-methoxypyridin-2-yl)benzoic acid (Compound 1) and the salt is 1:1.

Another aspect of the present invention provides the crystalline salt as an anhydrous crystalline salt of Compound 1 (Form 1).

Another aspect of the present invention provides the crystalline salt as a trihydrate crystalline salt of Compound 1 (Form 2).

Another aspect of the present invention provides Form 1, wherein Form 1 has a PXRD pattern comprising peaks at diffraction angles of 9.6, 10.7, and 11.3 2θ, ±0.2° 2θ.

Another aspect of the present invention provides Form 1, wherein Form 1 has a PXRD pattern comprising peaks, as expressed as 2θ, substantially the same as shown in FIG. 1.

Another aspect of the present invention provides Form 1, wherein Form 1 has a Raman spectrum comprising peak shifts at 1511, 1561, and 1615 cm$^{-1}$, ±2 cm$^{-1}$.

Another aspect of the present invention provides Form 1, wherein Form 1 has a Raman spectrum comprising peak shifts at 989, 1218, 1511, 1561, and 1615 cm$^{-1}$, ±2 cm$^{-1}$.

Another aspect of the present invention provides Form 1, wherein Form 1 has a Raman spectrum comprising peak shifts at 568, 698, 989, 1218, 1511, 1561, and 1615 cm$^{-1}$, ±2 cm$^{-1}$.

Another aspect of the present invention provides Form 1, wherein Form 1 has a Raman spectrum comprising peak shifts, expressed as cm$^{-1}$, substantially the same as shown in FIG. 2.

Another aspect of the present invention provides Form 1, wherein Form 1 has a $^{13}$C ssNMR spectrum comprising chemical shifts at 22.9, 146.2, and 161.9 ppm, ±0.2 ppm.

Another aspect of the present invention provides Form 1, wherein Form 1 has a $^{13}$C ssNMR spectrum comprising chemical shifts at 22.9, 146.2, 157.9, 161.9, and 172.9 ppm, ±0.2 ppm.

Another aspect of the present invention provides Form 1, wherein Form 1 has a $^{13}$C ssNMR spectrum comprising chemical shifts, expressed as ppm, substantially the same as shown in FIG. 3.

Another aspect of the present invention provides Form 1, wherein Form 1 has an analytical parameter selected from the group consisting of a Raman spectrum comprising peak shifts at 1561 and 1615 cm$^{-1}$, ±2 cm$^{-1}$, and a $^{13}$C ssNMR spectrum comprising at least one chemical shift at 22.9, 146.2, or 161.9 ppm, ±0.2 ppm.

Another aspect of the present invention provides Form 1, wherein Form 1 has an analytical parameter selected from the group consisting of a Raman spectrum comprising peak shifts at 1511 and 1615 cm$^{-1}$, ±2 cm$^{-1}$, and a $^{13}$C ssNMR spectrum comprising at least one chemical shift at 22.9, 146.2, or 161.9 ppm, ±0.2 ppm.

Another aspect of the present invention provides Form 1, wherein Form 1 has an analytical parameter selected from the group consisting of a Raman spectrum comprising peak shift at 1615 cm$^{-1}$, ±2 cm$^{-1}$, and a $^{13}$C ssNMR spectrum comprising at least one chemical shift at 22.9, 146.2, or 161.9 ppm, ±0.2 ppm.

Another aspect of the present invention provides Form 1, wherein Form 1 has an analytical parameter selected from the group consisting of a Raman spectrum comprising peak shift at 1561 cm$^{-1}$, ±2 cm$^{-1}$, and a $^{13}$C ssNMR spectrum comprising at least one chemical shift at 22.9, 146.2, or 161.9 ppm, ±0.2 ppm.

Another aspect of the present invention provides Form 1, wherein Form 1 has an analytical parameter selected from the group consisting of a $^{13}$C ssNMR spectrum comprising chemical shifts at 22.9 and 161.9 ppm, ±0.2 ppm, and a Raman spectrum comprising at least one peak shift at 1511, 1561, or 1615 cm$^{-1}$, ±2 cm$^{-1}$.

Another aspect of the present invention provides Form 1, wherein Form 1 has an analytical parameter selected from the group consisting of a $^{13}$C ssNMR spectrum comprising chemical shifts at 146.2 and 161.9 ppm, ±0.2 ppm, and a Raman spectrum comprising at least one peak shift at 1511, 1561, or 1615 cm$^{-1}$, ±2 cm$^{-1}$.

Another aspect of the present invention provides Form 1, wherein Form 1 has an analytical parameter selected from the group consisting of a PXRD pattern comprising peaks at diffraction angles of 9.6 and 10.7 2θ, ±0.2° 2θ, and a Raman spectrum comprising at least one peak shift at 1511, 1561, or 1615 cm$^{-1}$, +2 cm$^{-1}$.

Another aspect of the present invention provides Form 1, wherein Form 1 has an analytical parameter selected from the group consisting of a PXRD pattern comprising peaks at diffraction angles of 9.6 and 10.7 2θ, ±0.2° 2θ, and a $^{13}$C ssNMR spectrum comprising at least one chemical shift at 22.9, 146.2, or 161.9 ppm, ±0.2 ppm.

Another aspect of the present invention provides Form 2, wherein Form 2 has a PXRD pattern comprising peaks at diffraction angles of 8.4, 9.0, 10.5 2θ, ±0.2° 2θ. Another aspect of the present invention provides Form 2, wherein Form 2 has a PXRD pattern comprising peaks at diffraction angles of 8.4, 9.0, 10.5, 15.0, and 24.7 2θ, ±0.2° 2θ.

Another aspect of the present invention provides Form 2, wherein Form 2 has a PXRD pattern comprising peaks, as expressed as 2θ, substantially the same as shown in FIG. 4.

Another aspect of the present invention provides Form 2, wherein Form 2 has a Raman spectrum comprising peak shifts at 1507, 1557, and 1610 cm$^{-1}$, ±2 cm$^{-1}$.

Another aspect of the present invention provides Form 2, wherein Form 2 has a Raman spectrum comprising peak shifts at 984, 1225, 1507, 1557, and 1610 cm$^{-1}$, ±2 cm$^{-1}$.

Another aspect of the present invention provides Form 2, wherein Form 2 has a Raman spectrum comprising peak shifts at 562, 692, 984, 1225, 1507, 1557, and 1610 cm$^{-1}$, ±2 cm$^{-1}$.

Another aspect of the present invention provides Form 2, wherein Form 2 has a Raman spectrum comprising peak shifts, expressed as cm$^{-1}$, substantially the same as shown in FIG. 5.

Another aspect of the present invention provides Form 2, wherein Form 2 has a $^{13}$C ssNMR spectrum comprising chemical shifts at 19.2, 149.5, and 163.8 ppm, ±0.2 ppm.

Another aspect of the present invention provides Form 2, wherein Form 2 has a $^{13}$C ssNMR spectrum comprising chemical shifts at 19.2, 149.5, 155.6, 163.8, and 188.3 ppm, ±0.2 ppm.

Another aspect of the present invention provides Form 2, wherein said Form 2 has a $^{13}$C ssNMR spectrum comprising chemical shifts, expressed as ppm, substantially the same as shown in FIG. 6.

Another aspect of the present invention provides Form 2, wherein Form 2 has an analytical parameter selected from the group consisting of
- a PXRD pattern comprising peaks at diffraction angles of 8.4 and 9.0 2θ, ±0.2° 2θ;
- a Raman spectrum comprising peak shifts at 1557 and 1610 cm$^{-1}$, ±2 cm$^{-1}$; and
- a $^{13}$C ssNMR spectrum comprising at least one chemical shift at 19.2, 149.5, or 163.8 ppm, ±0.2 ppm.

Another aspect of the present invention provides Form 2, wherein Form 2 has an analytical parameter selected from the group consisting of
- a PXRD pattern comprising peaks at diffraction angles of 8.4 and 10.5 2θ, ±0.2° 2θ;
- a Raman spectrum comprising peak shifts at 1507 and 1610 cm$^{-1}$, ±2 cm$^{-1}$; and
- a $^{13}$C ssNMR spectrum comprising at least one chemical shift at 19.2, 149.5, or 163.8 ppm, ±0.2 ppm.

Another aspect of the present invention provides Form 2, wherein Form 2 has an analytical parameter selected from the group consisting of a Raman spectrum comprising a peak shift at 1557 cm$^{-1}$, ±2 cm$^{-1}$; and a $^{13}$C ssNMR spectrum comprising at least one chemical shift at 19.2, 149.5, or 163.8 ppm, ±0.2 ppm.

Another aspect of the present invention provides Form 2, wherein Form 2 has an analytical parameter selected from the group consisting of a Raman spectrum comprising peak shift at 1610 cm$^{-1}$, ±2 cm$^{-1}$; and a $^{13}$C ssNMR spectrum comprising at least one chemical shift at 19.2, 149.5, or 163.8 ppm, ±0.2 ppm.

Another aspect of the present invention provides Form 2, wherein Form 2 has an analytical parameter selected from the group consisting of a $^{13}$C ssNMR spectrum comprising chemical shifts at 19.2 and 149.5 ppm, ±0.2 ppm; and a Raman spectrum comprising at least one peak shift at 1507, 1557, or 1610 cm$^{-1}$, ±2 cm$^{-1}$.

Another aspect of the present invention provides Form 2, wherein Form 2 has an analytical parameter selected from the group consisting of a $^{13}$C ssNMR spectrum comprising chemical shifts at 149.5 and 163.8 ppm, ±0.2 ppm; and a Raman spectrum comprising at least one peak shift at 1507, 1557, or 1610 cm$^{-1}$, ±2 cm$^{-1}$.

Another aspect of the present invention provides Form 2, wherein Form 2 has an analytical parameter selected from the group consisting of a PXRD pattern comprising peaks at diffraction angles of 8.4 and 9.0 2θ, ±0.2° 2θ; and a Raman spectrum comprising at least one peak shift at 1507, 1557, or 1610 cm$^{-1}$, ±2 cm$^{-1}$.

Another aspect of the present invention provides Form 2, wherein Form 2 has an analytical parameter selected from the group consisting of a PXRD pattern comprising peaks at diffraction angles of 8.4 and 9.0 2θ, ±0.2° 2θ; and a $^{13}$C ssNMR spectrum comprising at least one chemical shift at 19.2, 149.5, or 163.8 ppm, ±0.2 ppm.

The invention also includes:
- a crystalline salt of Compound 1, including Form 1 and/or Form 2, as described herein, for use as a medicament;
- a method comprising administering to a mammal a therapeutically effective amount of the crystalline salt of Compound 1, including Form 1 and/or Form 2, to treat diseases including NAFLD, NASH, and T2D; and
- use of a crystalline salt of Compound 1, including Form 1 and/or Form 2, as described herein, for the manufacture of a medicament for treating diseases including NAFLD, NASH, and T2D.

A further aspect of the present invention provides a pharmaceutical composition comprising Form 1 or Form 2 as described herein. In a further aspect, the invention provides an oral dosage form comprising Form 1 or Form 2, or any one of the pharmaceutical compositions described herein. For example, in one embodiment the oral dosage form is a tablet, pill or capsule. For example, in one embodiment, the oral dosage form is a tablet or capsule.

The dosage regimen for the compounds of the invention and/or compositions containing said compounds is based on a variety of factors, including the type, age, weight, sex and medical condition of the patient; the severity of the condition; the route of administration; and the activity of the particular compound employed. Thus, the dosage regimen may vary widely. For a normal adult human having a body weight of about 100 kg, a typical daily dosage amount is in the range of from about 0.001 mg to about 10 mg per kilogram body weight is typically sufficient, preferably from about 0.01 mg/kg to about 5.0 mg/kg, more preferably from about 0.01 mg/kg to about 1 mg/kg. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

In another aspect, the invention comprises pharmaceutical compositions. Such pharmaceutical compositions comprise Form 1 or Form 2 with a pharmaceutically acceptable carrier. Other pharmacologically active substances can also be present. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof, and may include isotonic agents, for example, sugars, sodium chloride, or polyalcohols such as mannitol, or sorbitol in the composition. Pharmaceutically acceptable substances such as wetting agents or minor amounts of auxiliary substances such as wetting or emulsifying agents, preservatives or buffers, which enhance the shelf life or effectiveness of the antibody or antibody portion.

Oral administration of a solid dose form may be, for example, presented in discrete units, such as hard or soft capsules, pills, cachets, lozenges, or tablets, each containing a predetermined amount of at least one compound of the invention. In another embodiment, the oral administration may be in a powder or granule form. In another embodiment, the oral dose form is sub-lingual, such as, for example, a lozenge. In such solid dosage forms, the compounds of Formula I are ordinarily combined with one or more adjuvants. Such capsules or tablets may contain a controlled release formulation. In the case of capsules, tablets, and pills, the dosage forms also may comprise buffering agents or may be prepared with enteric coatings.

EXAMPLES

In the preparation of Compound 1, it is noted that some of the preparation methods described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T.W. Greene, Protective Groups in Organic Synthesis, John Wiley & Sons, New York, 1991. Furthermore, this invention is not limited to specific synthetic methods provided herein that may vary.

Intermediate 1: 1-Isopropyl-4,6-dihydrospiro[indazole-5,4'-piperldin]-7(1H)-one, hydrochloride salt

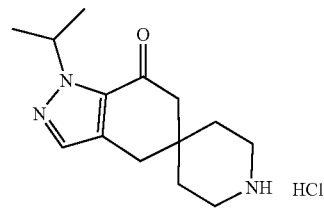 [SMILES: CC(C)n1ncc2c1C(=O)CC1(CCNCC1)C2 ; Cl]

Step 1. tert-Butyl 9-oxo-3-azaspiro[5.5]undec-7-ene-3-carboxylate

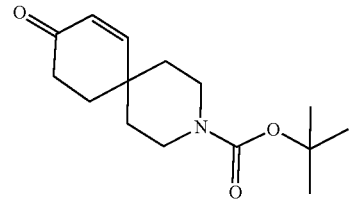 [SMILES: CC(C)(C)OC(=O)N1CCC2(C=CC(=O)CC2)CC1]

A dry reactor was charged with tert-butyl 4-formylpiperidine-1-carboxylate (108 Kg), cyclohexane (1080 L) and pyrrolidine (64.8 Kg) at 25-30° C. The mixture was stirred 5-10 min, and was then heated to reflux for 12-16 h, while collecting water using a Dean-Stark trap. The reaction mixture was then cooled to 50-60° C., at which temperature vacuum was applied to distill excess pyrrolidine and cyclohexane. The reaction mixture was then cooled to 25-30° C., and cyclohexane (648 L) was charged, followed by methyl vinyl ketone (49.63 Kg). The mixture was stirred for 12-16 h, then filtered and the filtrate was charged into a clean and dry reactor. The solution was cooled to 10-15° C., then a solution of acetic acid (54.75 Kg) in water (54 L) was slowly added, maintaining the temperature below 15° C. At the end of the addition, the mixture was warmed up to 25-30° C. and stirred for 12-16 h. The layers were separated and the aqueous was extracted with ethyl acetate (324 L). Combined organic layers were washed with a solution of sodium bicarbonate (32.34 Kg) in water (324 L), then dried over sodium sulfate. The solids were washed with ethyl acetate (54 L), and combined filtrates were concentrated under reduced pressure at below 40° C. n-Heptane (216 L) was charged into the reactor and distillation was pursued under reduced pressure and at below 40° C. until dryness. The mixture was cooled to 25-30° C. and n-heptane (216 L) was charged in the reactor. The mixture was stirred for 1-2 h after formation of solids. The solids were then filtered, washed with n-heptane (54 L) and dried at 40-50° C. for 10-12 h to generate the desired material (90.1 Kg, 67% yield).

Step 2. (E)-tert-Butyl 10-((dimethylamino)methylene)-9-oxo-3-azaspiro[5.5]undec-7-ene-3-carboxylate

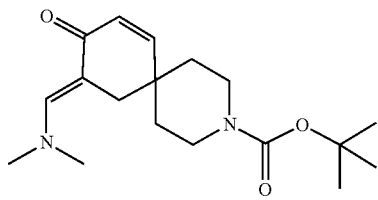 [SMILES: CN(C)/C=C1\CC2(C=CC1=O)CCN(C(=O)OC(C)(C)C)CC2]

A clean and dry reactor was charged with tert-butyl 9-oxo-3-azaspiro[5.5]undec-7-ene-3-carboxylate (50 Kg), N,N-dimethylformamide (500 L) and N,N-dimethylformamide dimethyl acetal (135 Kg) at 25-30° C. under nitrogen atmosphere. The reaction mixture was stirred 5-10 min then heated to 120-130° C. for 20 h. the mixture was then cooled to 50-60° C., and the solvent was distilled under high vacuum at below 60° C. Mix-xylenes (200 L) was charged at below 45° C. and the solvent was distilled under high vacuum at below 60° C. This operation was repeated with another lot of mix-xylenes (200 L). Toluene (200 L) was then charged into the reactor and the solvent was distilled under high vacuum at below 60° C. This operation was repeated with a second lot of toluene (200 L). Methyl tert-butyl ether (100 L) was then charged at below 30° C. and the solvent was distill under high vacuum at below 40° C. The mixture was cooled down to 15-20° C. and methyl tert-butyl ether (100 L) was charged at below 20° C. The mixture was stirred for 20-30 min and the solids were filtered, washed with methyl tert-butyl ether (50 L) and dried without vacuum at 50-55° C. for 10 h to provide the desired compound (52.1 Kg, 87% yield). $^1$H NMR (400 MHz, CDCl$_3$) δ ppm 7.48 (s, 1H), 6.57 (d, J=9.97 Hz, 1H), 5.99 (d, J=10.16 Hz, 1H), 3.32-3.51 (m, 4H), 3.06 (s, 6H), 2.72 (s, 2H), 1.57-1.66 (m, 2H), 1.41-1.53 (m, 11H).

Step 3. tert-Butyl 1-isopropyl-1,4-dihydrospiro[indazole-5,4'-piperidine]-1'-carboxylate

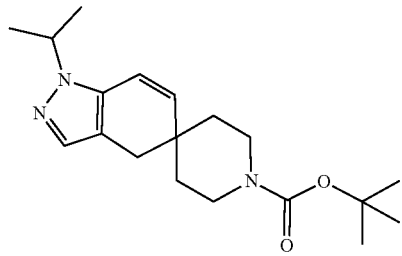 [SMILES: CC(C)n1ncc2c1C=CC1(CCN(C(=O)OC(C)(C)C)CC1)C2]

A clean and dry reactor was charged with (E)-tert-butyl 10-((dimethylamino)methylene)-9-oxo-3-azaspiro[5.5]undec-7-ene-3-carboxylate (80 Kg), toluene (704 L) and trimethylamine (16 L) at 25-30° C. The reaction mixture was warmed up to 70-80° C., and a solution of isopropyl hydrazine hydrochloride salt in methanol (1.25 equiv., 141 Kg total) was added over 4-5 h. The reaction mixture was then stirred for 8-10 h at 70-80° C., prior cooling to 15-25° C. A solution of citric acid (48 Kg) in water (480 L) was then slowly added, maintaining internal temperature below 25° C. Ethyl acetate (208 L) was added and the mixture was stirred for 10 min. Layers were separated and the organic layer was successively washed with a solution of citric acid (48 Kg) in water (480 L), then with only water (320 L). Combined aqueous layers were extracted with ethyl acetate (320 L). Combined organic layers were then dried over sodium sulfate (8 Kg) and the solvents were evaporated to dryness under reduce pressure and at below 40° C. Dichloromethane (240 L) was charged into the reactor and the mixture was stirred at 25-30° C. until clear. Activated carbon (1.84 Kg), magnesium silicate (1.84 Kg) and silica gel (32 Kg, 100-200 mesh) were successively charged at 25-30° C. and the heterogeneous mixture was stirred for 1 h. The slurry was then filter on a Hyflow bed, prepared by mixing Hyflow supercell (8 Kg) and dichloromethane (40 L). The cake was washed with dichloromethane (three times 120 L). The combined filtrates were charged back in the reactor and the solvent was evaporated under reduced pressure at below 40° C. n-Heptane (160 L) was then charged and distilled under reduced pressure at below 40° C. n-Heptane (200 L) was charged in the reactor and the mixture was cooled down to 0-5° C. After stirring for 12-15 h, the solids were filtered at 0° C., washed with chilled (0-5° C.) n-heptane (160 L) and dried under vacuum at 40-50° C. to provide the title compound (82.4 Kg, 75%). $^1$H NMR (400 MHz, CDCl$_3$) δ ppm 7.25 (s, 1H), 6.42 (dd, J=10.05, 0.49 Hz, 1H) 5.84 (d, J=9.95 Hz, 1H), 4.42-4.52 (m, 1H), 3.36-3.53 (m, 4H), 2.62 (s, 2H) 1.56-1.68 (m, 2H) 1.45-1.55 (m, 17H).

Step 4. 1-Isopropyl-4,6-dihydrospiro[indazole-5,4'-piperldin]-7(1H)-one, hydrochloride salt

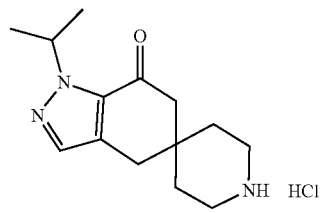 [SMILES: CC(C)n1ncc2c1C(=O)CC1(CCNCC1)C2 ; Cl]

A clean and dry reactor was charged with tert-butyl 1-isopropyl-1,4-dihydrospiro[indazole-5,4'-piperidine]-1'-carboxylate (60 Kg) and methanol (600 L) at 25-30° C. N-Bromosuccinimide (32.4 Kg) was added in 5 portions over 30-40 min at 25-30° C. and stirring was continued for 30-60 min. A solution of sodium thiosulfate pentahydrate (5.4 Kg) in water (102 L) was slowly added, maintaining internal temperature below 30° C. The mixture was stirred for 20-30 min then the solvent was evaporated under reduced pressure at below 45° C. The residue was cooled down to 25-30° C. and 2-methyltetrahydrofuan (420 L) was charged in the reactor, along with water (90 L). The mixture was stirred for 15-20 min, then the layers were separated, the aqueous layer was further extracted with 2-methyltetrahydrofuran (120 L). Combined organic extracts were treated for 15-20 min at 25-30° C. with a solution of sodium hydroxide (4.8 Kg) in water (120 L). Layers were separated and the organic layer was washed with water (120 L), followed by a solution of sodium chloride (12 Kg) in water (120 L) and then dried over sodium sulfate (6 Kg). After filtration, the cake was washed with 2-methyltetrahydrofuran (30 L) and combined filtrate were charged back into the reactor. The solvent was completely distilled at below 45° C. under reduced pressure and the residue was solubilized in tetrahydrofuran (201 L). In another clean and dry reactor was charged potassium tert-butoxide (60.6 Kg) and tetrahydrofuran (360 L) at 25-30° C. To that mixture was slowly added the solution of the residue in tetrahydrofuran maintaining a temperature below 30° C. The reaction mixture was then warmed up to 60-65° C. and kept at this temperature for 1-2 h. Upon completion, the mixture was cooled to 0-10° C., and slowly quenched with a solution of hydrochloric acid (1 N, 196 L), maintaining internal temperature below 10° C. The reaction mixture was allowed to warm up to 25-30° C., and ethyl acetate (798 L) was charged. After stirring for 15-20 min, the layers were separated, and the aqueous layer was further extracted with ethyl acetate (160 L). Combined organic layers were washed with water (160 L), dried over sodium sulfate (8 Kg), filtered, and the cake was washed with ethyl acetate (300 L). The solvents were entirely distilled under reduced pressure at below 45° C., and ethyl acetate (540 L) was charged into the reactor at 25-30° C., followed by methanol (156 L). The mixture was cooled to 0-5° C., at which point acetyl chloride (79.8 Kg) was slowly added, maintaining the temperature in the specified range. The mixture was then allowed to warm up to 20-25° C. and was kept at this temperature for 4-5 h with stirring. The resulting slurry was filtered and the solids were washed with ethyl acetate (120 L), then dried at 40-45° C. for 8-10 h to furnish the desired crude product (33.5 Kg, 65%).

A final purification step was performed by solubilizing this crude solid (56.8 Kg) in methanol (454.4 L) in a clean a dried reactor at 25-30° C. The solution was stirred for 30-45 min, then passed through a 0.2 micron cartridge filter into a clean and dry reactor at 25-30° C. Methanol was distilled under reduced pressure at below 50° C. until ~1 vol solvent remains. The reaction mixture was cooled to 25-30° C. and fresh acetonitrile (113.6 L) was charged through a 0.2 micron cartridge filter. The solvents were distilled under reduced pressure at below 50° C. until ~1 vol solvent remains. The reaction mixture was cooled to 25-30° C. and fresh acetonitrile (190 L) was charged into the reactor through a 0.2 micron cartridge filter. The mixture was warmed up to 65-70° C. and stirred for 45 min, then cooled down to 25-30° C. and stirred for 1 h. the resulting slurry was filtered, and the cake was washed with chilled (15° C.) acetonitrile (56.8 L). The solids were dried under reduced pressure at 40-50° C. for 8 h to afford Intermediate 1 (36.4 Kg, 64%). $^1$H NMR (400 MHz, CD$_3$OD) δ ppm 7.43 (s, 1H), 5.32-5.42 (m, 1H), 3.15-3.25 (m, 4H), 2.89 (s, 2H), 2.64 (s, 2H), 1.69-1.90 (m, 4H), 1.37-1.45 (m, 6H); ESI [M+H]$^+$=248.

Intermediate 2: 2-(4-(tert-Butoxycarbonyl)phenyl)-6-methoxyisonicotinic acid

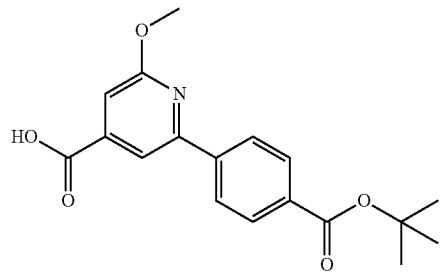 [SMILES: COc1cc(C(=O)O)cc(-c2ccc(C(=O)OC(C)(C)C)cc2)n1]

A clean and dried reactor was charged with 2,6-dichloroisonicotinic acid (30 Kg) and methanol (120 L) at 20-25° C. The slurry was stirred for 5 min then heated up to 65° C. (reflux). A solution of sodium methoxide in methanol (30%, 87.2 Kg) was then slowly charged over at least 4 h via addition funnel. The funnel was rinsed with methanol (15 L), and stirring was pursued at 65° C. for at least 15 h. the mixture was then cooled down to 45° C. and distilled under reduced pressure until a residual volume of ~90 L. A solution of potassium bicarbonate (28.2 Kg) and potassium carbonate (21.6 Kg) in water (180 L) was then charged into the reactor at 40-45° C. The reactor containing the aqueous solution was rinsed with water (21 L) and the wash was charged into the reaction mixture. The mixture was distilled under reduced pressure at below 80° C. until a residual volume of ~240 L, then cooled down to 20-25° C.

Another clean and dry reactor was charged with tert-butyl 4-(4,4,5,5-tetramethyl-1,3,2-dioxoborolan-2-yl) benzoate (52.3 Kg) and dioxane (340 Kg), and stirred at 2-25° C. until complete dissolution. The content of the former reactor was then heated at 40° C. to ensure complete solubility and transferred into this new reactor. The reaction mixture was cooled down to 20-25° C., and a deoxygenation step was performed via vacuum/nitrogen cycles. The mixture was further cooled down to 0-10° C. and palladium acetate (0.65 Kg) was charged into the reactor followed by triphenylphosphine (2.46 Kg) under nitrogen flow. The mixture was warmed up to 20-25° C. and another deoxygenation step was performed via vacuum/nitrogen cycles. The mixture was then heated to 80° C. and maintained at this temperature for at least 18 h. the mixture was cooled down to 20-25° C., then methyl tert-butyl ether (133.2 Kg) and water (30 L) were successively charged into the reactor. The layers were separated, and the aqueous was diluted with water (110 L), then extracted with methyl tert-butyl ether (110 L). Combined organic extracts were washed with a solution of citric acid (52 Kg) in water (84 L), and the layers were separated. The aqueous layer was further extracted with methyl tert-butyl ether (88.8 Kg) and organic layers were combined, then washed three times with a third of a solution of sodium chloride (43 Kg) in water (80 L). After final layer separation, the organic layer was filtered through pall filter containing a charcoal cartridge, and the cake was washed with methyl tert-butyl ether (11.2 Kg). The filtrate was distilled under reduced pressure at below 50° C. down to ~90 L, and was then successively co-distilled with heptane (120 L), at below 50° C. and down to ~120 L. the mixture was then cooled down to 20-25° C. over 1 h, then stirred at this temperature for another 1 h. The slurry was filtered and the cake was washed three times with heptane (3×18 L), then three times with acetonitrile (3×18 L). The resulting wet solid was dried under vacuum and nitrogen flow at below 45° C. for at least 15 h to afford Intermediate 2 (44.6 Kg, 87% yield). $^1$H NMR (400 MHz, CDCl$_3$) δ ppm 8.13 (s, 2H), 8.09 (s, 2H), 7.97 (d, J=1.17 Hz, 1H), 7.34 (d, J=0.98 Hz, 1H), 4.08 (s, 3H), 1.61 (s, 9H); ESI [M+H]$^+$=330.

Intermediate 3: tert-Butyl 4-(4-(1-isopropyl-7-oxo-1,4,6,7-tetrahydrospiro[indazole-5,4'-piperidine]-1'-carbonyl)-6-methoxypyridin-2-yl)benzoate

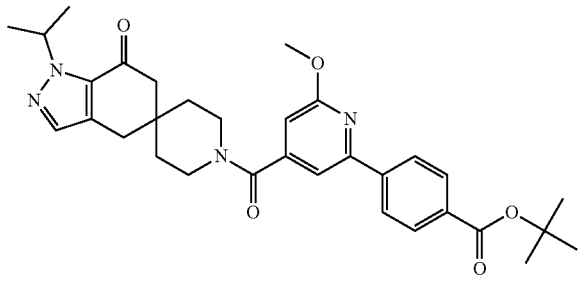 [SMILES: COc1cc(C(=O)N2CCC3(CC2)CC(=O)c2c(cnn2C(C)C)C3)cc(-c2ccc(C(=O)OC(C)(C)C)cc2)n1]

A round bottomed flask was charged with 2-(4-(tert-butoxycarbonyl)phenyl)-6-methoxyisonicotinic acid (Intermediate 2, 15.2 g, 46.2 mmol) and ethyl acetate (140 mL). 1,1'-Carbonyldiimidazole (8.98 g, 55.4 mmol) was added in one portion and stirred for 1 h at rt. 1-isopropyl-4,6-dihydrospiro[indazole-5,4'-piperldin]-7(1H)-one hydrochloride (Intermediate 1, 14.8 g, 52.2 mmol) was added followed by N,N-diisopropylethylamine (9.1 mL, 52.2 mL) and the reaction stirred for 18 h at rt. Aqueous 2 M HCl (40 mL) was added, followed by 1 M potassium hydrogensulfate (40 mL) and 50 mL of heptane. The obtained mixture was stirred for 1 h at rt. The mixture was transferred to separation funnel. The organic phase was separated, washed successively with water (20 mL), saturated sodium bicarbonate (30 mL), water (20 mL), brine (20 mL), dried over 20 g of magnesium sulfate and 10 g of silica gel, filtered, and concentrated in vacuo. Solid began to form towards the end of concentration. The residue was stirred in 40 mL of ethyl acetate at 80° C. and heptane (120 mL) was added slowly dropwise. The mixture was stirred at 80° C. for 1 h, then slowly cooled to room temperature with stirring over 1 h and stirred for 18 h at rt. The solid was collected via filtration, washed with water and ethyl acetate-heptane (1:3), and dried under vacuum at 50° C. for 18 h to obtain Intermediate 3 (19.64 g, 76% yield).

Alternative Preparation of Intermediate 3

A clean and dry reactor was charged with acetonitrile (219 Kg) and 2-(4-(tert-butoxycarbonyl)phenyl)-6-methoxyisonicotinic acid (Intermediate 2, 34.8 Kg) at 20-25° C. The mixture was stirred for 5 min, then 1,1-carbodiimidazole (18.9 Kg) was charged in three successive portions. The slurry was further stirred at 20-25° C. for at least 1 h, then 1-isopropyl-4,6-dihydrospiro[indazole-5,4'-piperldin]-7(1H)-one hydrochloride salt (Intermediate 1, 33.0 Kg) was charged into the reactor, followed by N,N-diisopropylethylamine (20.5 Kg) via pump. The reagent pump as well as the walls of the reactor were washed with acetonitrile (13.7 Kg), and stirring was pursued at 20-25° C. for at least 2 h. Upon completion, the mixture was seeded with tert-butyl 4-(4-(1-isopropyl-7-oxo-1,4,6,7-tetrahydrospiro[indazole-5,4'-piperidine]-1'-carbonyl)-6-methoxypyridin-2-yl)benzoate (Intermediate 3, 209 g) and stirred for at least 30 min. After confirmation of crystallization start, a solution of citric acid monohydrate (58.5 Kg) in water (257 L) was charged over 1 h. The resulting slurry was further stirred at 20-25° C. for at least 2 h, then filtered and the cake was washed with a mixture of acetonitrile (68.4 Kg) and water (87 L). This wash was used to rinse the reactor as well. The solids were dried under reduced pressure at below 55° C., affording Intermediate 3 (43.44 Kg, 73% yield).

Compound 1 (as the Free Acid): 4-(4-(1-isopropyl-7-oxo-1,4,6,7-tetrahydrospiro[indazole-5,4'-piperidine]-1'-carbonyl)-6-methoxypyridin-2-yl)benzoic acid

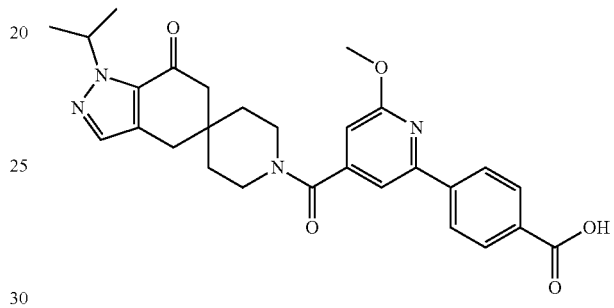

A round bottomed flask was charged with tert-butyl 4-(4-(1-isopropyl-7-oxo-1,4,6,7-tetrahydrospiro[indazole-5,4'-piperidine]-1'-carbonyl)-6-methoxypyridin-2-yl)benzoate (3.7 g, 6.6 mmol) and toluene (25 mL). 85% Phosphoric acid (3.0 mL) was added dropwise with stirring and the reaction was heated to 60° C. for 4 hours. A colorless thick gum formed. The reaction was cooled to rt and water was added. White solids were observed. The toluene organic layer was discarded, reserving the aqueous layer and solids. Ethyl acetate was added (60 mL) and 4N NaOH solution was added to adjust pH to ~7. The layers were separated and the aqueous was extracted with ethyl acetate (50 mL). The combined ethyl acetate organic layers were dried over sodium sulfate, filtered, and concentrated in vacuo to provide white solids. These were dissolved in ethyl acetate (80 mL) at 50° C. and heptane (90 mL) was added slowly. The heat was removed and the mixture was cooled to rt and stirred for 16 h. The resultant solids were collected via filtration, rinsed with the mother liquor, and dried to provide the title compound (Compound 1 free form, 2.15 g, 65% yield) as a white solid.

Alternative Preparation of Compound 1 (as the Free Acid)

A clean a dry reactor was charged with acetonitrile (130.4 Kg) and tert-butyl 4-(4-(1-isopropyl-7-oxo-1,4,6,7-tetrahydrospiro[indazole-5,4'-piperidine]-1'-carbonyl)-6-methoxypyridin-2-yl)benzoate (Intermediate 3, 20.72 Kg) at 20-25° C. The mixture was stirred for 5 min, then p-toluenesulfonic acid (8.5 Kg) was charged under a gentle nitrogen sweep. The reaction mixture was warmed up to 70° C. and maintained at this temperature for at least 6.5 h. Upon completion, the mixture was cooled down to 40° C., seeded with Compound 1 (104 g) and water (83 L) was slowly charged over at least 1 h. the mixture was further stirred at 40° C. for a minimum of 4 h, then cooled down to 20-25° C. over 2 h. Further stirring for at least 2 h was followed by filtration, and the cake was rinsed with a solution of acetonitrile (33 Kg) and water (41 L). This wash was used to rinse the reactor as well. The resulting solids were dried under reduced pressure at below 55° C. to afford Compound 1 (16.5 Kg, 89% yield).

Preparation of Form 1—Anhydrous mono-tris of Compound 1

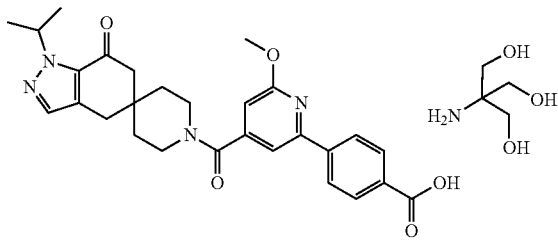 [SMILES: COc1cc(C(=O)N2CCC3(CC2)CC(=O)c2c(cnn2C(C)C)C3)cc(-c2ccc(C(=O)O)cc2)n1 ; NC(CO)(CO)CO]

A vial was charged with 4-(4-(1-isopropyl-7-oxo-1,4,6,7-tetrahydrospiro[indazole-5,4'-piperidine]-1'-carbonyl)-6-methoxypyridin-2-yl)benzoic acid (151 mg, 0.300 mmol) and 3 mL of ethanol. The mixture was heated to 80° C. for 5 minutes to dissolve the solid and then cooled to rt. Tris(hydroxymethyl)aminomethane (39 mg, 0.32 mmol) was added, and the mixture was stirred overnight at rt. Heptane (2.25 mL) was added dropwise to produce a slurry that was heated to 50° C. to produce a clear solution. The mixture was cooled to rt overnight with stirring. White solids were observed, and the mixture was stirred for an additional 3 days. The material was filtered and dried in a vacuum oven at 50° C. overnight to produce Form 1 (151 mg, 0.242 mmol, 81% yield).

Alternative Preparation of Form 1: Anhydrous mono-tris of Compound 1

To a clean and dry reactor was charged ethanol (83 L), followed by the addition of Compound 1 (9.43 Kg) and tris (2.55 kg) while the mixture was maintained at a temperature of 20-25° C. The tank walls were rinsed with ethanol (2 L), and the resulting mixture was heated at 65-70° C., maintained at this temperature for at least 30 min until all solids dissolved, then cooled down to 45-50° C. A warm filtration through a 10 μm in-line polypropylene filter was performed, and the reactor as well as the filter were washed with ethanol (9 L). n-Heptane (24 L) was charged into the warm solution through the same in-line filter, and the mixture was seeded with 4-(4-(1-isopropyl-7-oxo-1,4,6,7-tetrahydrospiro[indazole-5,4'-piperidine]-1'-carbonyl)-6-methoxypyridin-2-yl) benzoic acid anhydrous tris salt (100 g) in ethanol (0.5 L) at 45-50° C. The temperature was held for at least 2 h before cooling down to 20-25° C. over at least 2 h. Stirring was pursued for at least 5 days. The slurry was then filtered, and the cake was washed with a mixture of ethanol (13 L) and n-heptane (6 L). The solids were dried under reduced pressure at below 45° C. for at least 12 h, affording example 1 (11.7 Kg, 77%).

Preparation of Form 2—Trihydrate of the mono-tris Salt of Compound 1

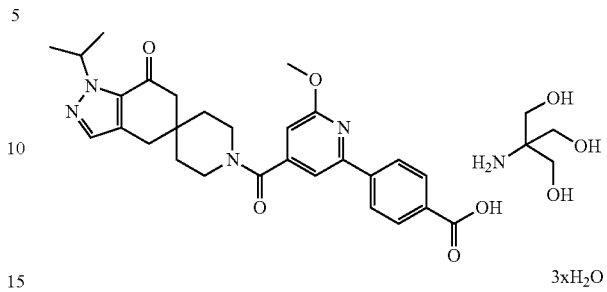

Form 2 was obtained from conversion from Form 1. Into a 50 mL EasyMax reactor was added Form 1 (1.7214 g, 2.760 mmol), Isopropanol (16.50 mL, 215.8 mmol), and Water (688 μL, 38.190 mmol). The mixture was stirred (300 rpm) for about 72 hr with a reactor jacket temperature of 25° C. The reaction mixture was then warmed to 40° C. over 15 min and held at 40° C. for about 24 hours, cooling once to 20° C. to remove a sample for testing. A mixture of forms was seen by PXRD; therefore, additional water Water (688 μL, 38.190 mmol) was added. The stir rate was increased to 400 rpm and the slurry was allowed to stir for 6 hours and was then cooled to 15° C. The solids were isolated on a 60 mL/40 M filter and washed with 96/4 isopropanol/water. The resulting material was consistent with Form 2 by PXRD.

Alternative Preparation of Form 2—Trihydrate of the mono-tris Salt of Compound 1

A clean and dry reactor was charged with isopropanol (60.4 Kg), and Compound 1 (16.68 Kg) and tris (4.42 kg) were added while the mixture was maintained at a temperature of 20-25° C. The mixture was stirred for 5 min, then water (6.7 Kg) was charged and the slurry was warmed up to 55° C. The now clear solution was filtered into a pre-warmed clean and dry reactor (50-55° C.) through an in-line 10 μm polypropylene filter. The solution was then seeded with the mono-tris salt of Compound 1 as a trihydrate (167 g). After verification that the seed persisted, the mixture was cooled down to 15° C. over at least 2 h, then maintained at 15° C. for a minimum of 16 h. The slurry was filtered and the cake washed with chilled isopropanol (13.1 Kg). The solids were then dried under reduced pressure at below 25° C. to afford only Form 2 (22.1 Kg, 98% yield).

Figure 7:
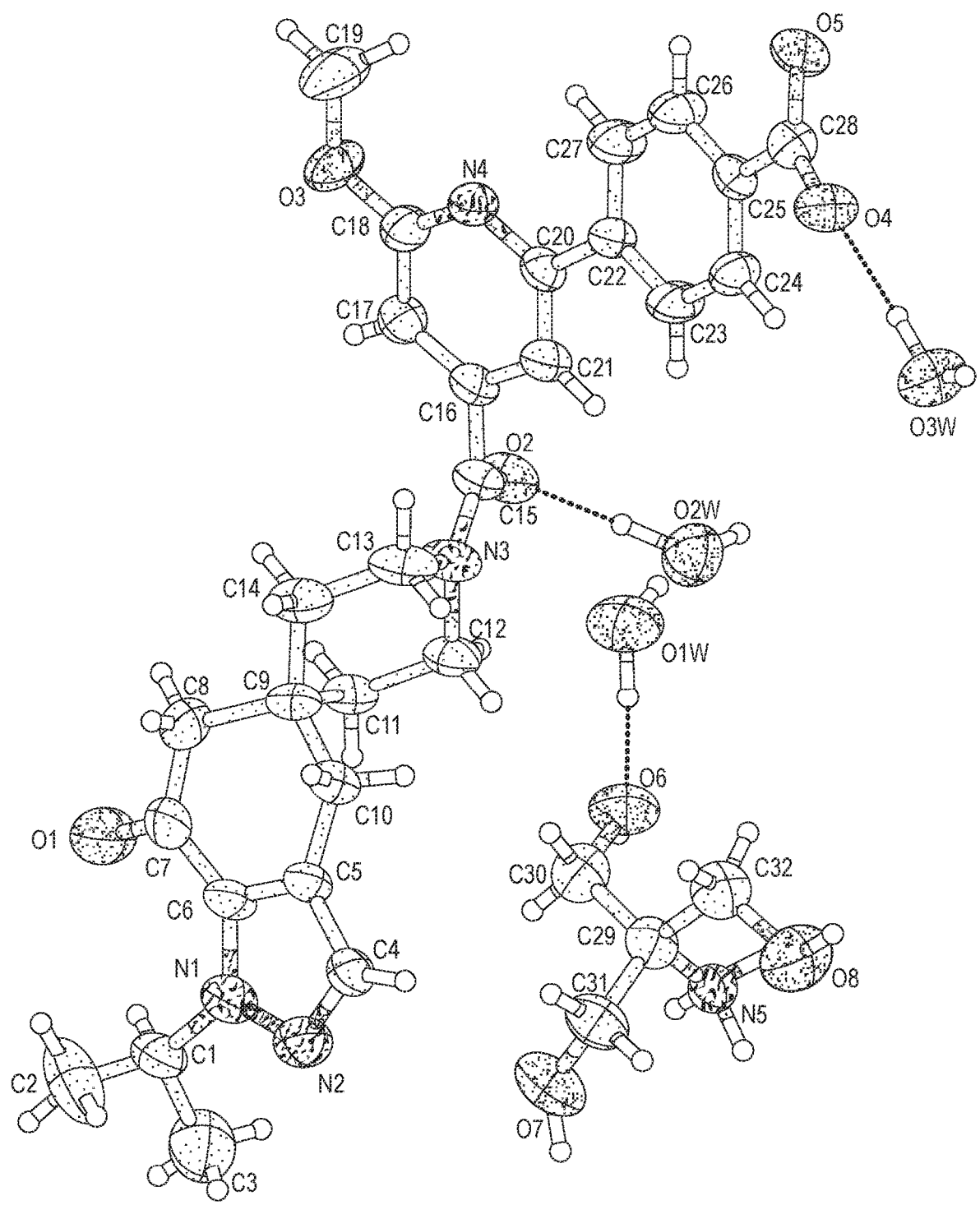
FIG. 7 shows an illustrative single crystal structure of Form 2.

To confirm the presence of three water molecules in Form 2, data was collected using a Bruker D8 Venture diffractometer at room temperature. See FIG. 7. The structure was solved by intrinsic phasing using SHELX software suite in the Monoclinic class space group P2$_1$/c (Version 5.1, Bruker AXS, 1997). The structure was subsequently refined by the full-matrix least squares method. All non-hydrogen atoms were found and refined using anisotropic displacement parameters.

The hydrogen atoms located on nitrogen and oxygen were found from the Fourier difference map and refined with distances restrained. The remaining hydrogen atoms were placed in calculated positions and were allowed to ride on their carrier atoms.

The final R-index was 7.2%. A final difference Fourier revealed no missing or misplaced electron density.

Table 10 provides data collected with regard to Form 2:

TABLE 10

| Empirical formula | $C_{28}H_{30}N_4O_5 \cdot C_4H_{11}NO_3 \cdot 3H_2O$ |
|---|---|
| Formula weight | 677.74 |
| Temperature | RT |
| Wavelength | 1.54178 Å |
| Crystal system | Monoclinic |
| Space group | $P2_1/c$ |
| Unit cell dimensions | a = 17.6927(9) Å  α = 90°. |
| | b = 13.2753(7) Å  β = 92.451(3)°. |
| | c = 14.6480(8) Å  γ = 90°. |
| Volume | 3437.3(3) Å$^3$ |
| Z | 4 |
| Density (calculated) | 1.310 Mg/m$^3$ |
| Goodness-of-fit on F$^2$ | 1.053 |
| Final R indices [I > 2sigma(I)] | R1 = 0.0723, wR2 = 0.1835 |
| R indices (all data) | R1 = 0.1244, wR2 = 0.2110 |

Pharmacokinetic Studies:

Pharmacokinetic studies were conducted in male (fasted) cynomolgus monkeys (n=2 for each formulation). An oral pill was prepared to compare Form 1 and Form 2. Separately, to compare the tris salt of Compound 1 and the free acid of Compound 1, a suspension was prepared. The dosage was administered as an oral dose containing 2, 5, or 10 mg/kg, respectively. Serial blood samples were collected at the 0, 0.25, 0.5, 1, 2, 4, 7, and 24-hour time points via the femoral vein by syringe and transferred into K$_3$EDTA vacutainers. Blood samples were then centrifuged, the plasma harvested and stored at −20° C. or −80° C. until analysis.

Solid Tablet for Oral Administration:

The oral tablets were prepared by mixing Form 1 or Form 2 with a standard blend of excipients that contained: 64% by weight of microcrystalline cellulose (Avicel PH102), 32% by weight of lactose monohydrate (Fast Flo 316), 3% by weight of sodium starch glycolate (Explotab®) and 1% by weight of magnesium stearate. The appropriate amount of either Form 1 or Form 2 was transferred into a mortar. The corresponding amount of the excipient blend was then geometrically added to the mortar and mixed thoroughly with the respective Form 1 or Form 2 using a pestle. The mixture was transferred to a container, and blended on a Turbula mixer for 5 minutes to provide a blend containing the respective Form 1 or Form 2 mixed with the excipients. For Form 1, the blend contained 19% by weight of Form 1 and 81% by weight of the excipient blend. For Form 2, the blend contained 21% by weight of Form 2 and 79% by weight of the excipient blend.

To prepare tablets, each blend was transferred to a Korsch XP-1 single-station press equipped with 0.2362" standard round concave tooling. The tablets were compressed to achieve 100 mg tablet weight, with target tablet hardness between 4 and 9 kp at the press speed of 15 tablets per minute.

Suspension for Oral Administration:

To prepare a representative batch size of 1 L of 0.5% (w/v) methylcellulose (Methocel® A4M) solution, approximately 0.4 L of deionized water was heated to 80-90° C. after which 5 grams of methylcellulose (Methocel® A4M) was added and mixed thoroughly until the particles were thoroughly wetted. The mixture was then removed from heat. Cold water (0.6 L) was then added, while continuously stirring in the ice bath, until all the methylcellulose particles were dissolved.

A 10 mg/mL Suspension of Compound 1 Prepared from the Free Acid:

The free acid of Compound 1 (220 mg) was transferred into a mortar. The solid powder was triturated (lumps broken) using a pestle. Two mL of 0.5% w/v methylcellulose (Methocel® A4M) was added to the powder drop-wise. The vehicle and free acid were well mixed to form a smooth paste. The remaining of the vehicle was added in small aliquots while mixing until a uniform suspension was obtained. The suspension was transferred to a 30 mL glass bottle using dropper and made up the volume of 22 mL to achieve the concentration of 10 mg/mL of the free acid of Compound 1. The pH was measured to be 6.04. Twenty-two microliter of Polysorbate 80 (Tween® 80) was added to the suspension. The formulation of 10 mg/mL of the free acid of Compound 1 in 0.5% w/v methylcellulose (Methocel® A4M), 0.1% v/v Polysorbate 80 (Tween® 80) was obtained.

A 2.5 mg/mL Suspension of Compound 1, Prepared from Tris Salt of Compound 1:

Form 1 (157 mg) was transferred to a mortar. The solid powder was triturated (lumps broken) using a pestle. Small amount of 0.5% w/v methylcellulose (Methocel® A4M) was added to the powder to form a smooth paste. The remaining of the vehicle was added in small aliquots while mixing until a uniform suspension was obtained. The suspension was transferred to a container and made up to final volume of 50 mL. A few clumps were observed, but a light suspension was obtained after stirring for approximately 1 hour.

Analytical Data:

Hygroscopicity:

Hygroscopicity was measured using a dynamic vapor sorption instrument manufactured by TA Instruments or Surface Measurement Systems. A sample of each Form was exposed to incremental RH levels until either a weight equilibrium (seen as a plateau) of ≤0.001% weight change in 5 minutes was met, or a maximum time of 120 minutes at each RH level. After the shorter of 0.001% weight equilibrium in 5 minutes or 120 minutes, the sample was then exposed to the next RH level. There was an initial drying period where weight may have been lost with Form 1, no drying was utilized for Form 2. The process starts at 10% RH with RH increased to 20% RH and then a 10% RH increase after each interval (0.001% in 5 minutes equilibrium or 120 min, whichever occurred first). At 90% RH, the RH was reversed back to 10% RH using the same equilibration criteria. The hygroscopicity is measured as a function of the percent weight gain measured at 90% RH. Form 1 has a hygroscopicity of about 1% at 90% RH/25° C. Form 2 also has a hygroscopicity of about 1% at 90% RH/25° C.

Thermodynamic Solubility Provided in Table 2:

Compound 1 as the free acid or the salt identified in Table 2 was received as dry powders and pre-weighed into Whatman Mini-Uniprep syringeless filter devices with 0.45 μm polytetrafluoroethylene (PTFE) membranes. Four hundred fifty microliters (450 μL) of the desired medium was added to the filter and agitated for 24 hours at RT. After 24 hours, the sample was filtered and the filtrates were injected into a nitrogen detector for quantification.

Buffer Preparation:

pH 1.2: Weigh out 1.0 g of NaCl and transfer to a beaker. Add about 450 mL HPLC-grade water to dissolve the NaCl. Titrate the solution to pH 1.2 with 36.6% HCl. Transfer the solution to a 500 mL volumetric flask and bring to 500 mL with HPLC-grade water.

pH 6.5: Titrate about 250 mL of 50 mM NaPO$_4$ dibasic with about 500 mL of 50 mM NaPO$_4$ monobasic to pH 6.5. The ending total volume is the volume at the point the solution has a pH 6.5 is reached when adding 50 mM NaPO$_4$ monobasic to the 50 mM NaPO$_4$ dibasic.

pH 7.4: Titrate about 200 mL of 50 mM NaPO$_4$ dibasic with about 50 mL of 50 mM NaPO$_4$ monobasic to pH 7.4. The ending total volume is the volume at the point the solution has a pH 7.4 is reached when adding 50 mM NaPO$_4$ monobasic to the 50 mM NaPO$_4$ dibasic.

Powder X-Ray Diffraction:

Powder X-ray diffraction analysis was conducted using a Bruker AXS D4 Endeavor diffractometer equipped with a Cu radiation source. The divergence slit was set at 0.6 mm while the secondary optics used variable slits. Diffracted radiation was detected by a PSD-Lynx Eye detector. The X-ray tube voltage and amperage were set to 40 kV and 40 mA respectively. Data was collected in the Theta-2Theta goniometer at the Cu (k-alpha average) from 3.0 to 40.0 degrees 2-Theta using a step size of 0.037 degrees and a time per step of 10 seconds. Samples were prepared by placing them in a silicon low background sample holder and rotated during collection. Data were collected using Bruker DIF-FRAC Plus software and analysis was performed by EVA diffract plus software (version 4.2.1). The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked and peak positions were adjusted to the peak maximum. Peaks with relative intensity of 3% were generally chosen. The peaks which were not resolved or were consistent with noise were not selected. A typical error associated with the peak position from PXRD stated in USP up to +/−0.2° 2-Theta (USP-941).

FT-Raman:

Raman spectra were collected using a Nicolet NXR FT-Raman accessory attached to the FT-IR bench. The spectrometer is equipped with a 1064 nm Nd:YVO4 laser and a liquid nitrogen cooled Germanium detector. Prior to data acquisition, instrument performance and calibration verifications were conducted using polystyrene. Samples of Form 1 or Form 2 were analyzed in glass NMR tubes that were static during spectral collection. Tablet samples were collected in a tablet sample holder which analyzed one spot on an intact tablet. The spectra were collected using 0.5 W of laser power and 512 co-added scans. The collection range was 3700-100 cm$^{-1}$. These spectra were recorded using 2 cm$^{-1}$ resolution and Happ-Genzel apodization. Utilizing the Raman method above, the possible variability associated with a spectral measurement is ±2 cm$^{-1}$. The samples (both neat API and drug product) were collected at ambient conditions (~23° C. and between 30%-60% RH). Form 1 should be stored with desiccant, while Form 2 may be stored at ambient conditions (15-30° C. and ambient humidities).

The intensity scale was normalized to 1 prior to peak picking. Peaks were manually identified using the Thermo Nicolet Omnic 9.7.46 software. Peak position was picked at the peak maximum, and peaks were only identified as such, if there was a slope on each side; shoulders on peaks were not included. For Form 1 or Form 2, an absolute threshold of 0.004 to 0.017 with a sensitivity of 80 was utilized during peak picking. The peak position has been rounded to the nearest whole number using standard practice (0.5 rounds up, 0.4 rounds down). Peaks with normalized peak intensity between (1-0.75), (0.74-0.30), (0.29-0) were labeled as strong, medium and weak, respectively.

Solid State NMR:

Solid state NMR (ssNMR) analysis was conducted on a Bruker-BioSpin CPMAS probe positioned into a Bruker-BioSpin Avance III 500 MHz ($^1$H frequency) NMR spectrometer. Form 1 material was packed into a 4 mm rotor sealed with a standard drive cap, and its spectrum was collected at ambient temperature. Form 2 material was packed into a 4 mm rotor sealed with drive cap containing an o-ring to prevent dehydration. The Form 2 spectrum was collected at 25° C. (calibrated by the chemical shift of PbNO$_3$). The packed rotors were oriented at the magic angle and spun at 15.0 kHz. $^{13}$C ssNMR spectra were collected using a proton decoupled cross-polarization magic angle spinning (CPMAS) experiment. A phase modulated proton decoupling field of 80-90 kHz was applied during spectral acquisition. The cross-polarization contact time was set to 2 ms and the recycle delay to 10 seconds. The number of scans was adjusted to obtain an adequate signal to noise ratio. The carbon chemical shift scale was referenced using a $^{13}$C CPMAS experiment on an external standard of crystalline adamantane, setting its upfield resonance to 29.5 ppm (as determined from neat TMS).

Automatic peak picking was performed using Bruker-BioSpin TopSpin version 3.5 software. Generally, a threshold value of 5% relative intensity was used for preliminary peak selection. The output of the automated peak picking was visually checked to ensure validity and adjustments were manually made if necessary. Although specific $^{13}$C solid state NMR peak values are reported herein there does exist a range for these peak values due to differences in instruments, samples, and sample preparation. This is common practice in the art of solid state NMR because of the variation inherent in peak positions. A typical variability for a $^{13}$C chemical shift x-axis value is on the order of plus or minus 0.2 ppm for a crystalline solid. The solid state NMR peak heights reported herein are relative intensities. Solid state NMR intensities can vary depending on the actual setup of the CPMAS experimental parameters and the thermal history of the sample.

What is claimed is:

1. A crystalline 2-amino-2-(hydroxymethyl)propane-1,3-diol salt of 4-(4-(1-isopropyl-7-oxo-1,4,6,7-tetrahydrospiro[indazole-5,4'-piperidine]-1'-carbonyl)-6-methoxypyridin-2-yl)benzoic acid, wherein the crystalline salt is a trihydrate crystalline salt.

2. The crystalline salt of claim 1, wherein the ratio of 4-(4-(1-isopropyl-7-oxo-1,4,6,7-tetrahydrospiro[indazole-5,4'-piperidine]-t-carbonyl)-6-methoxypyridin-2-yl)benzoic acid and the salt is 1:1.

3. The trihydrate crystalline salt of claim 1, wherein said trihydrate crystalline salt has a PXRD pattern comprising peaks at diffraction angles of 8.4, 9.0, and 10.5 2θ, ±0.2° 2θ.

4. The trihydrate crystalline salt of claim 3, wherein said trihydrate crystalline salt has a Raman spectrum comprising peak shifts at 1507, 1557, and 1610 cm$^{-1}$, ±2 cm$^{-1}$.

5. The trihydrate crystalline salt of claim 4, wherein said trihydrate crystalline salt has a $^{13}$C ssNMR spectrum comprising chemical shifts at 19.2, 149.5, and 163.8 ppm, ±0.2 ppm.

6. The trihydrate crystalline salt of claim 1, wherein said trihydrate crystalline salt has an analytical parameter selected from the group consisting of
a PXRD pattern comprising peaks at diffraction angles of 8.4 and 9.0 2θ, ±0.2° 2θ,
a Raman spectrum comprising peak shifts at 1557 and 1610 cm$^{-1}$, ±2 cm$^{-1}$, and a $^{13}$C ssNMR spectrum comprising at least one chemical shift at 19.2, 149.5, or 163.8 ppm, ±0.2 ppm.

7. The trihydrate crystalline salt of claim 1, wherein said trihydrate crystalline salt has an analytical parameter selected from the group consisting of a PXRD pattern comprising peaks at diffraction angles of 8.4 and 9.0 2θ, ±0.2° 2θ, and a Raman spectrum comprising at least one peak shift at 1507, 1557, or 1610 cm$^{-1}$, ±2 cm$^{-1}$.

8. The trihydrate crystalline salt of claim 1, wherein said trihydrate crystalline salt has an analytical parameter selected from the group consisting of a PXRD pattern comprising peaks at diffraction angles of 8.4 and 9.0 2θ, ±0.2° 2θ, and a $^{13}$C ssNMR spectrum comprising at least one chemical shift at 19.2, 149.5, or 163.8 ppm, ±0.2 ppm.

9. The trihydrate crystalline salt of claim 1, where said trihydrate crystalline salt is substantially pure.

10. A pharmaceutical composition comprising the crystalline salt of claim 1 in a therapeutically effective amount with a pharmaceutically acceptable carrier.

11. A method of treating a disease selected from nonalcoholic fatty liver disease (NAFLD), nonalcoholic steatohepatitis (NASH), and type 2 diabetes (T2D) in a mammal, the method comprising administering to the mammal a therapeutically effective amount of the crystalline salt of claim 1.

* * * * *